United States Patent
Stobbe et al.

(10) Patent No.: US 10,543,068 B2
(45) Date of Patent: Jan. 28, 2020

(54) DENTAL DEVICES AND RELATED TECHNOLOGY

(71) Applicant: Nathan Stobbe, Salt Lake City, UT (US)

(72) Inventors: Nathan Stobbe, Salt Lake City, UT (US); Alesha Snell, Draper, UT (US); Jeff Stronk, Salt Lake City, UT (US)

(73) Assignee: Nathan Stobbe, Salt Lake City, UT (US)

( * ) Notice: Subject to any disclaimer, the term of this patent is extended or adjusted under 35 U.S.C. 154(b) by 51 days.

(21) Appl. No.: 15/089,796

(22) Filed: Apr. 4, 2016

(65) Prior Publication Data

US 2016/0317262 A1 Nov. 3, 2016

Related U.S. Application Data

(60) Provisional application No. 62/142,825, filed on Apr. 3, 2015, provisional application No. 62/170,949, filed on Jun. 4, 2015, provisional application No. 62/218,420, filed on Sep. 14, 2015, provisional application No. 62/253,349, filed on Nov. 10, 2015.

(51) Int. Cl.
| | | |
|---|---|---|
| *A61C 13/235* | (2006.01) | |
| *A61C 8/00* | (2006.01) | |
| *A61C 13/265* | (2006.01) | |
| *A61C 13/225* | (2006.01) | |

(52) U.S. Cl.
CPC .......... *A61C 13/235* (2013.01); *A61C 8/0027* (2013.01); *A61C 13/2656* (2013.01); *A61C 13/225* (2013.01)

(58) Field of Classification Search
CPC ... A61C 13/235; A61C 8/0027; A61C 8/0048; A61C 8/0081; A61C 8/0095; A61C 13/0004; A61C 13/12; A61C 13/225; A61C 13/2656
See application file for complete search history.

(56) References Cited

U.S. PATENT DOCUMENTS

| | | | | |
|---|---|---|---|---|
| 1,698,259 | A | * | 1/1929 | Craig ...................... A61C 13/26 433/181 |
| 4,184,252 | A | | 1/1980 | Krol et al. |
| 4,693,686 | A | | 9/1987 | Sendax |
| 4,741,698 | A | | 5/1988 | Andrews |
| 4,904,186 | A | * | 2/1990 | Mays .................... A61C 8/0048 433/172 |
| 5,630,717 | A | * | 5/1997 | Zuest ................... A61C 8/0048 433/172 |

(Continued)

OTHER PUBLICATIONS

International Written Opinion from International Application No. PCT/US2016/025898, dated Aug. 29, 2016, 4 pages.

(Continued)

*Primary Examiner* — Heidi M Eide
(74) *Attorney, Agent, or Firm* — TraskBritt

(57) ABSTRACT

The present disclosure is directed to denture devices and related technology. A device may include an overdenture including a substructure comprising at least one hinge. The device may further include a dental implant prosthesis configured to be attached to a jawbone and including at least one extensions configured for contacting the at least one hinge of the overdenture to secure the overdenture to the dental implant prosthesis.

7 Claims, 23 Drawing Sheets

(56) References Cited

U.S. PATENT DOCUMENTS

| | | | | |
|---|---|---|---|---|
| 5,662,653 A * | 9/1997 | Songer | ............... | A61B 17/7032 |
| | | | | 606/265 |
| 2002/0102514 A1 * | 8/2002 | Huffman | ................ | A61C 9/002 |
| | | | | 433/34 |
| 2004/0005530 A1 * | 1/2004 | Mullaly | ............... | A61C 8/0048 |
| | | | | 433/172 |
| 2005/0032024 A1 * | 2/2005 | Castellon | ............. | A61C 8/0048 |
| | | | | 433/172 |
| 2010/0143871 A1 * | 6/2010 | Berger | ............... | A61B 17/8605 |
| | | | | 433/174 |
| 2012/0064486 A1 | 3/2012 | Sobrado Marinho | | |
| 2012/0094253 A1 * | 4/2012 | Berger | ................ | A61C 8/0048 |
| | | | | 433/173 |
| 2016/0228220 A1 * | 8/2016 | Collins | ................ | A61C 8/0095 |

OTHER PUBLICATIONS

International Search Report from International Application No. PCT/US2016/025898, dated Aug. 29, 2016, 4 pages.

\* cited by examiner

DENTAL DEVICES AND RELATED TECHNOLOGY

CROSS-REFERENCE TO RELATED APPLICATIONS

This application claims the benefit of and priority to U.S. Provisional App. No. 62/142,825, filed Apr. 3, 2015, U.S. Provisional App. No. 62/170,949, filed Jun. 4, 2015, U.S. Provisional App. No. 62/218,420, filed Sep. 14, 2015, and U.S. Provisional App. No. 62/253,349, filed Nov. 10, 2015, each of which incorporated herein by reference.

TECHNICAL FIELD

This disclosure relates generally to dental devices, more specifically, to dentures and related technology.

BACKGROUND OF RELATED ART

Dentures, which are prosthetic devices made to replace missing teeth, are typically removable. Ordinary removable dentures comprise teeth mounted in a suitable plate or base. Although dentures are traditionally fitted for user, they are still prone to slippage and/or discomfort.

The subject matter claimed herein is not limited to embodiments that solve any disadvantages or that operate only in environments such as those described above. Rather, this background is only provided to illustrate one example technology area where some embodiments described herein may be practiced.

BRIEF SUMMARY

One specific embodiment includes a dental device. The dental device includes a bar configured to be attached to a jawbone. The bar includes at least one magnet proximate an outer, lateral surface. Further, the bar includes at least one distal extension extending from the lateral surface and configured for securing an overdenture thereto.

According to another specific embodiment, a dental device includes at least one abutment configured to couple to a jawbone. The abutment includes at least one magnet and at least one extension configured to at least partially secure an overdenture thereto.

According to another embodiment, a dental device includes an overdenture including a substructure comprising at least one hinge. The dental device further includes a dental implant prosthesis configured to be attached to a jawbone and including at least one extension configured for contacting the at least one hinge of the overdenture to secure the overdenture to the dental implant prosthesis. For example, the dental implant prosthesis may include a bar or at least one abutment.

Other aspects, as well as features and advantages of various aspects, of the present disclosure will become apparent to those of skill in the art through consideration of the ensuing description, the accompanying drawings and the appended claims.

DETAILED DESCRIPTION

Figure 1:
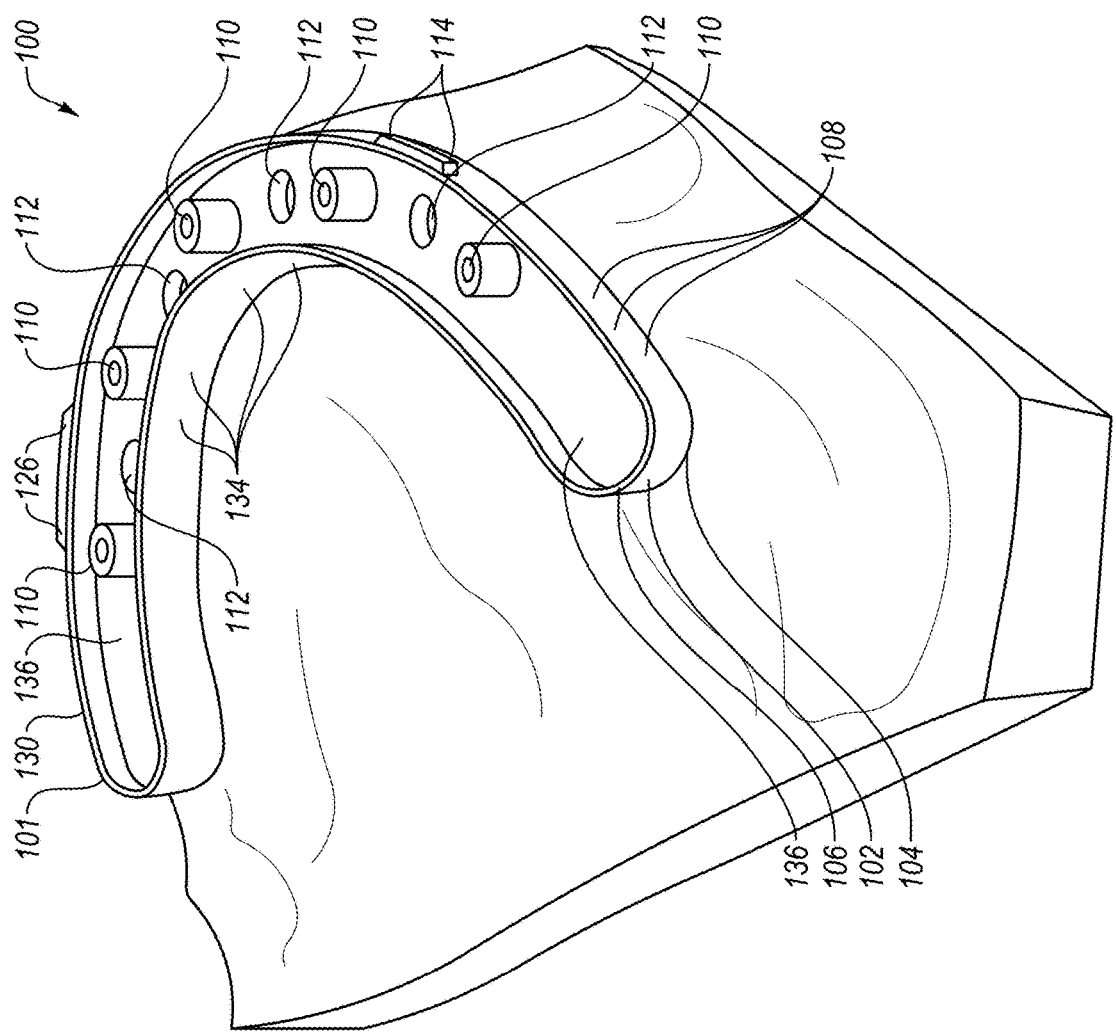
FIG. 1 depicts a dental implant prosthesis including a bar, according to an embodiment of the present disclosure.

Referring in general to the accompanying drawings, various embodiments of the present disclosure are illustrated to show structure. Common elements of the illustrated embodiments are designated with like numerals. It should be understood that the figures presented are not meant to be illustrative of actual views of any particular portion of the actual device structure, but are merely schematic representations which are employed to more clearly and fully depict embodiments of the disclosure.

The following provides a more detailed description of the present disclosure and various representative embodiments thereof. In this description, functions may be shown in block diagram form in order not to obscure the present disclosure in unnecessary detail. Additionally, block definitions and partitioning of logic between various blocks is exemplary of a specific implementation. It will be readily apparent to one of ordinary skill in the art that the present disclosure may be practiced by numerous other partitioning solutions. For the most part, details concerning timing considerations and the like have been omitted where such details are not necessary to obtain a complete understanding of the present disclosure and are within the abilities of persons of ordinary skill in the relevant art.

Various embodiments of the present disclosure relate to a versatile, easy-to-use denture device including a dental implant prosthesis (e.g., a bar or one or more abutments) and an overdenture. The overdenture, which is removable, may be retained in a patient's mouth magnetically, mechanically, or both. In one example, the overdenture may be secured to a dental implant prosthesis via one or more flexible flanges (i.e., that lock into one or more undercuts on a facial surface of the dental implant prosthesis), one or more bilateral distal extensions on the dental implant prosthesis, or any combination thereof. A denture device may not require implant screw access through a dental implant prosthesis, as opposed to the conventional screw retained fixed hybrid dentures.

In contrast to existing removable hybrid dentures that are retained by replaceable locator attachments using popular Dolder and Hader implant bars, various embodiments disclosed herein include magnets of varying strength to further secure an overdenture to a dental implant prosthesis. A dental implant prosthesis and an overdenture may each include one or more magnets housed therein. The magnets may be arranged such that the magnets (e.g., cylindrical, rectangular, cube, and/or square magnets) provide magnetic attraction between the dental implant prosthesis and the overdenture in a vertical and/or horizontal fashion. In some embodiments, replaceable and interchangeable magnets of varying strength may be used.

In one embodiment, a dental device may include a dental implant prosthesis (e.g., a bar or one or more abutments) and an overdenture, wherein the dental implant prosthesis and/or the overdenture may include one or more printable magnets, which may also be referred to as polymagnets. In this embodiment, the dental device may not require mechanical retention (e.g., distal extensions and distal hinges).

Moreover, some embodiments relate to dentures including technology (e.g., wearable technology). As non-limiting examples, the technology may include sensors, communication technology, location technology, etc. Other embodiments relate to scanning and drilling devices, which may be configured for attaching to a universal and removable guardrail. The guardrail may be attached to (e.g., removably screwed into) a facial surface of a dental implant prosthesis (e.g., a bar). The scanning and drilling device, which may be automated, removable, and programmable, may be configured for various operations, such as locating, scanning, and drilling on, for example, a patients' internal pressure sensor lined porcelain teeth. The scanning and drilling device may be compatible with various removable screw retained universal guardrails.

FIG. 1 depicts a dental implant prosthesis 100 including a bar 101, according to an embodiment of the present disclosure. It is noted that the term "bar" may also be referred to herein as a "bar prosthesis." Bar 101 includes an outer surface 102 of a distal wall, an apical aspect 104, a coronal aspect 106, an outer surface 108 of a facial wall, implant attachment devices (e.g., screws) 110, spaces 112 (e.g., for one or more magnets), a facial undercut 114, a facial undercut 126, an inner surface 130 of a facial wall, an outer surface 134 of a lingual wall, and a floor 136. Bar 101 may comprise any suitable materials, such as a metal (e.g. titanium). It is noted that one or more magnets may be inserted into bar 101 via an inferior surface/intaglio surface of bar 101.

As will be understood, a dental implant prosthesis (e.g., dental implant prosthesis 100) may be coupled (e.g., via one or more screws) to a jawbone (e.g., of a human). Further, as described more fully below, bar 101 may be configured to receive an overdenture, which may couple to bar 101 mechanically, magnetically, or both.

Figure 2:
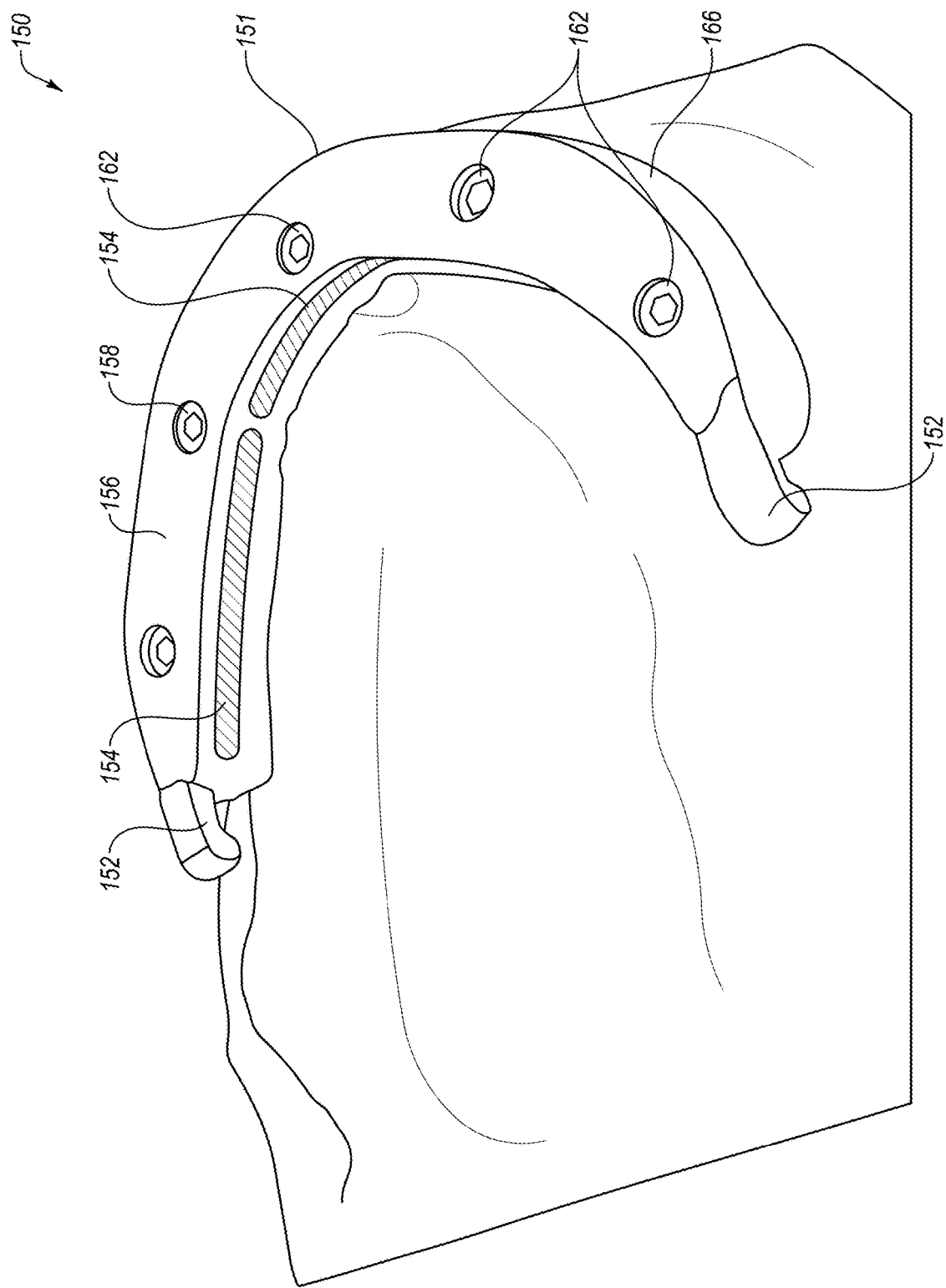
FIG. 2 is another illustration of a dental implant prosthesis including a bar, in accordance with an embodiment of the present disclosure.

FIG. 2 is another illustration of dental implant prosthesis 150 including a bar 151, in accordance with an embodiment of the present disclosure. Bar 151 includes extensions 152 at distal ends, wearable sensor technology (e.g., strips) 154, a superior aspect 156, an implant screw 158, implant attachments (e.g., screws) 162, and a facial surface 166. Bar 151 may also include one or more magnets (not shown in FIG. 2). It is noted that the term "extension" may also be referred to herein a "hinge" or an "undercut." As will be described more fully herein, extensions 152 may assist in retaining an overdenture in a mouth of a user. Stated another way, extensions 152 are configured to secure an overdenture to bar 101.

Figure 3:
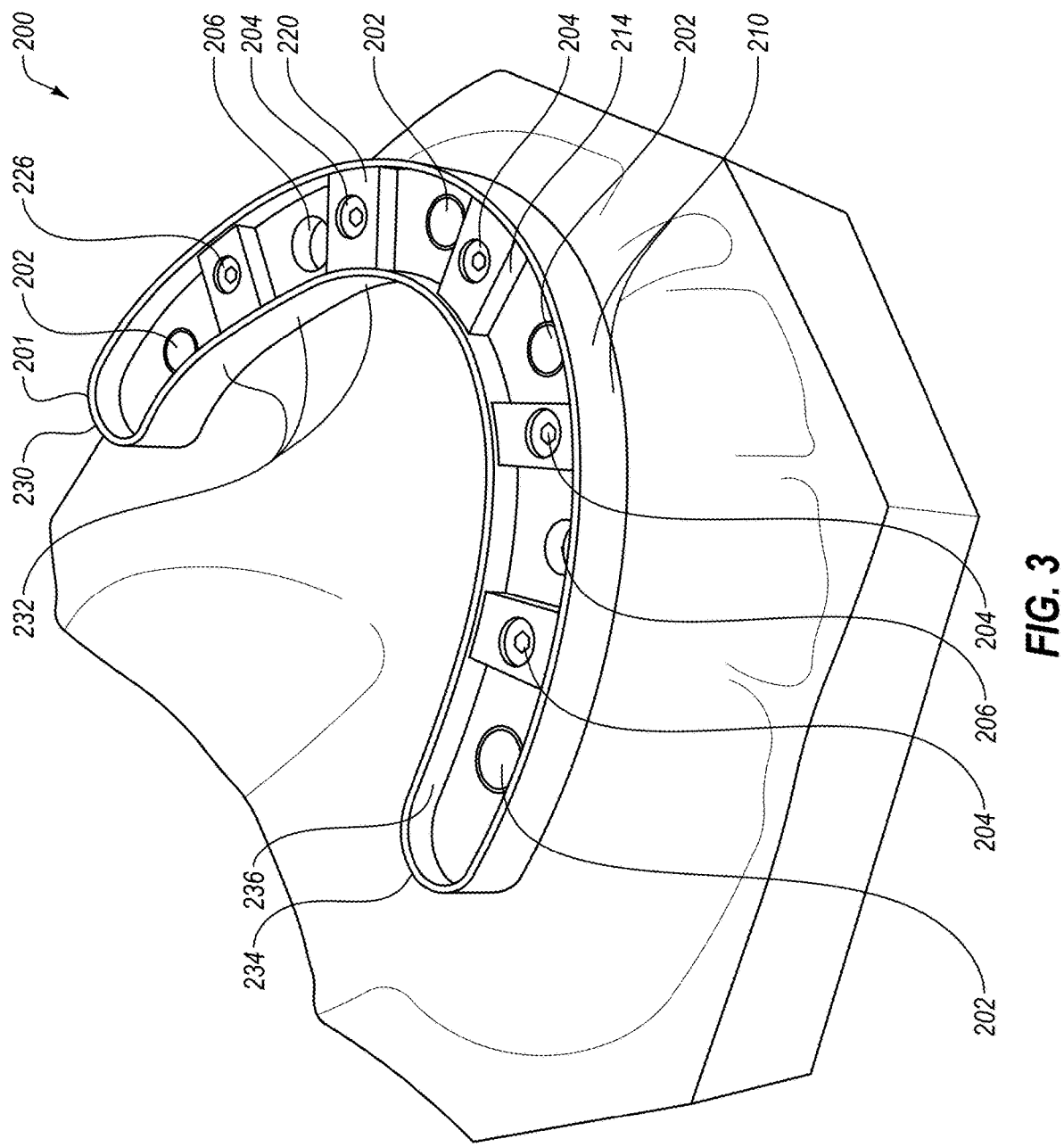
FIG. 3 is yet another illustration of a dental implant prosthesis including a bar, in accordance with an embodiment of the present disclosure.

FIG. 3 is yet another illustration of a dental implant prosthesis 200 including a bar 201, in accordance with an embodiment of the present disclosure. Bar 201 includes a magnet 202, an implant screw 204, space for magnet 206, an outer surface 210 of a facial wall, a wall (e.g., vertical wall) 214, a wall (e.g., vertical wall) 220, a hole 226 (e.g., for an implant screw), a distal wall 230, an outer surface 232 of a lingual wall, a distal wall 234, and an inner surface 236 of a lingual wall.

Figure 4A:
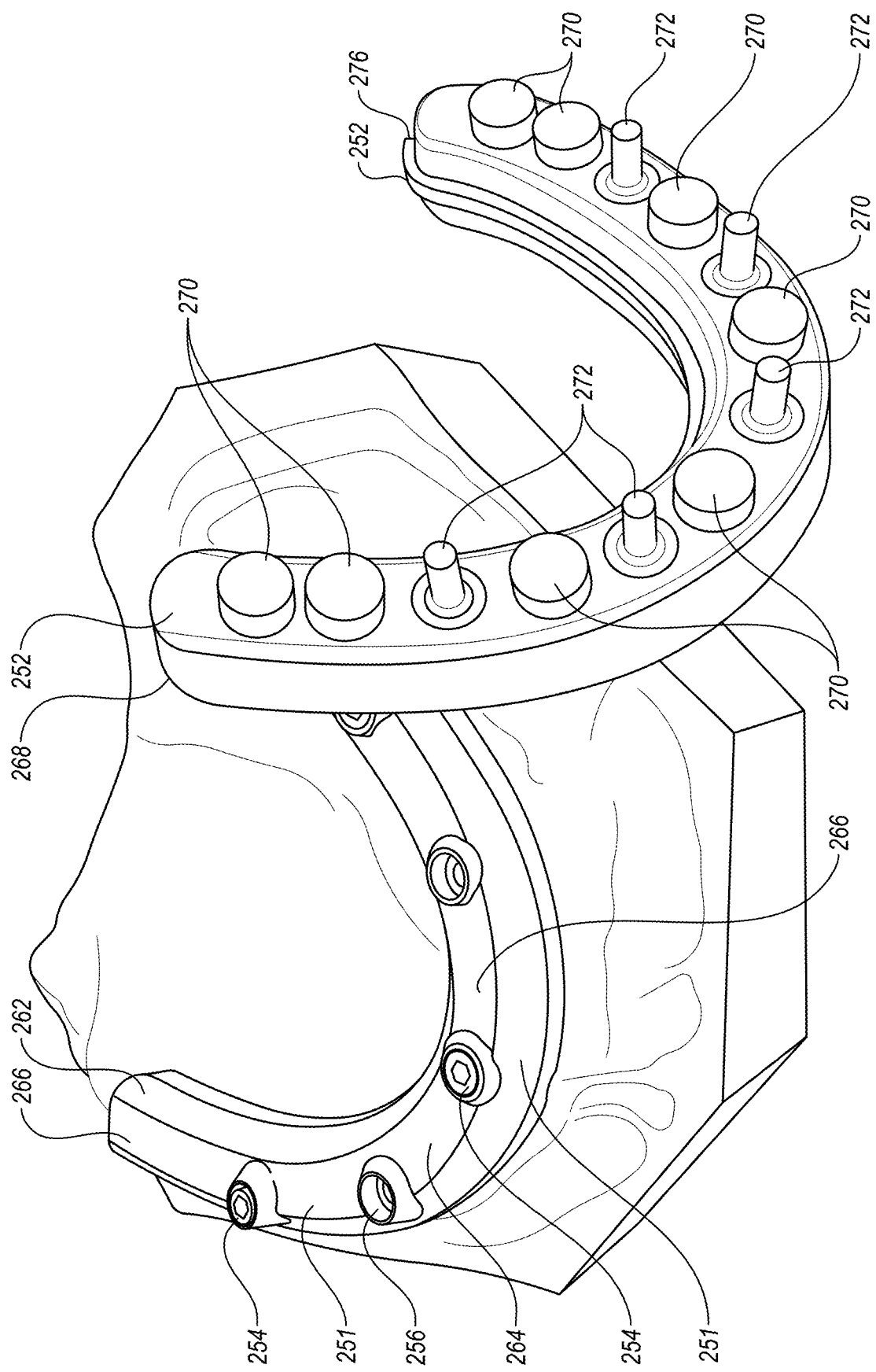
FIGS. 4A and 4B depict a dental implant prosthesis and an overdenture, according to an embodiment of the present disclosure.
Figure 4B:
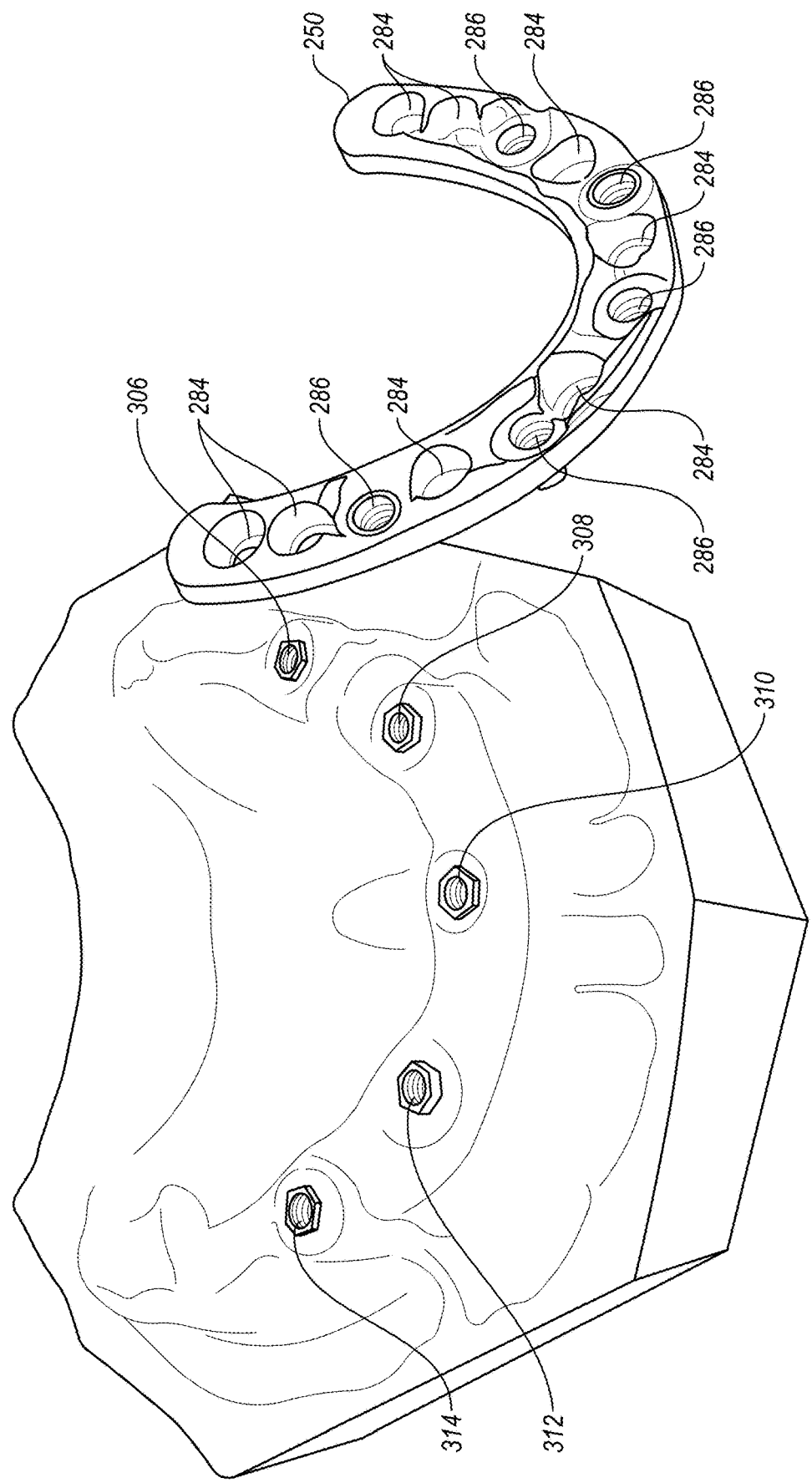

FIGS. 4A and 4B depict a bar 251 and a substructure 252, according to an embodiment of the present disclosure. As illustrated in FIG. 4A, bar 251 includes an implant screw 254, space 256 for an implant screw, a superior-lingual aspect 262, a superior aspect 264, a superior aspect 266. Further, substructure 252 includes an outer-lateral aspect 268, one or more magnets 270, vertical posts 272 (e.g., for increased retention & surface area of an overdenture), and a distal finish line 276. As illustrated in FIG. 4B, bar 250 includes a space 284 for a magnet and a space 286 for an implant screw. FIG. 4B further illustrates implants 306, 308, 310, 312, and 314.

Figure 5:
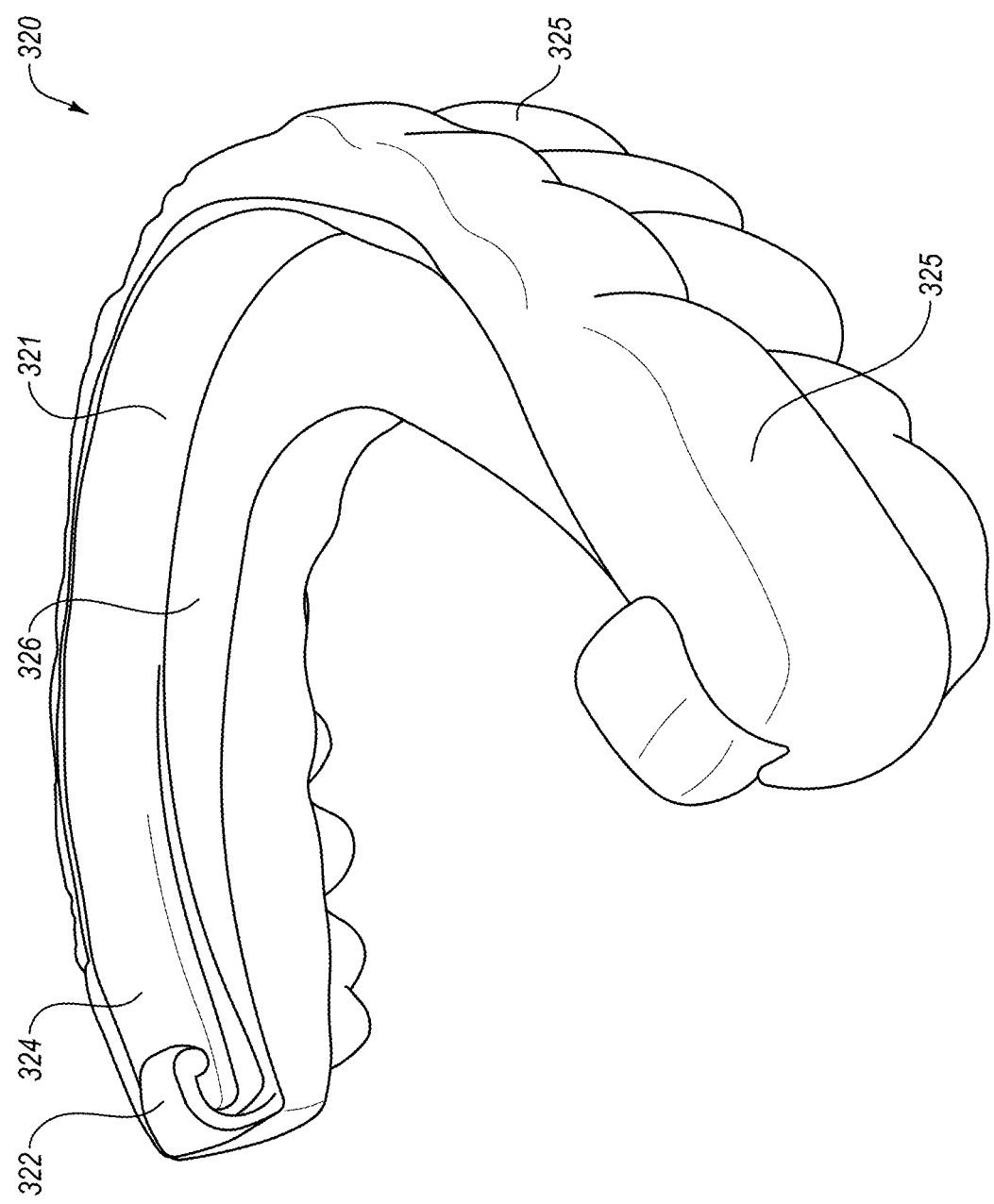
FIG. 5 illustrates an overdenture including a substructure, in accordance with an embodiment of the present disclosure.

FIG. 5 illustrates an overdenture 320 including a substructure 321 and teeth 325, in accordance with an embodiment of the present disclosure. Substructure 321 includes a hinge 322, an inferior-lateral surface 324, and an inferior surface 326. It is noted that substructure 321 may further include another hinge (not shown in FIG. 5) at another distal end of substructure 321. As will be appreciated, hinge 322, illustrated as having a hook-shape, may be configured to secure substructure 321 to either a bar (e.g., bar 151 (see FIG. 2) or bar 341 (see FIG. 6)) or an abutment (e.g. abutment 360; see FIG. 7). More specifically, hinge 322 may be configured to couple to an extension (e.g., extension 152; see FIG. 2) of a bar or an abutment to secure substructure 321 to the bar or the abutment.

An overdenture (e.g., overdenture 320) may include various materials such as, but not limited to, zirconia, porcelain, titanium, neodymium magnets, Pekkton®, pressed or injected acrylic, e.Max ceramic, acrylic resin, PMMA, 3D printed material, resin composite, bonding agent, amalgam, chromium cobalt, or any combination thereof. An inferior surface of an overdenture may include titanium, zirconia, PMMA, e.max ceramic, or Pekkton®, chromium cobalt, or any other FDA approved material. A substructure (e.g., substructure 321) may include, for example, a metal, such as titanium. Further, one or more magnets may be fixed (e.g., attached via glue) to a substructure, which may also include one or more vertical titanium posts to increase available bonding surface area and increase retention for the remaining denture (e.g., teeth) to be glued onto.

In one embodiment, one or more magnets may be inserted into an overdenture (e.g., substructure 321 or substructure 252) via an occlusal surface, or from an inferior intaglio surface, with or without the use of a titanium substructure designed to house the one or more magnets or provide strength and esthetics for the overdenture. If magnets are inserted into the overdenture from the occlusal surface, a space may remain in the overdenture such that the space may be "filled-in" with wearable technology (e.g., of dimensions of approximately 4.7625 mm in diameter and 4-6 mm in height) and/or acrylic resin material. Furthermore, it is noted the magnets in an overdenture and/or a prosthesis bar may or may not be visible (e.g., to a patient).

Figure 6:
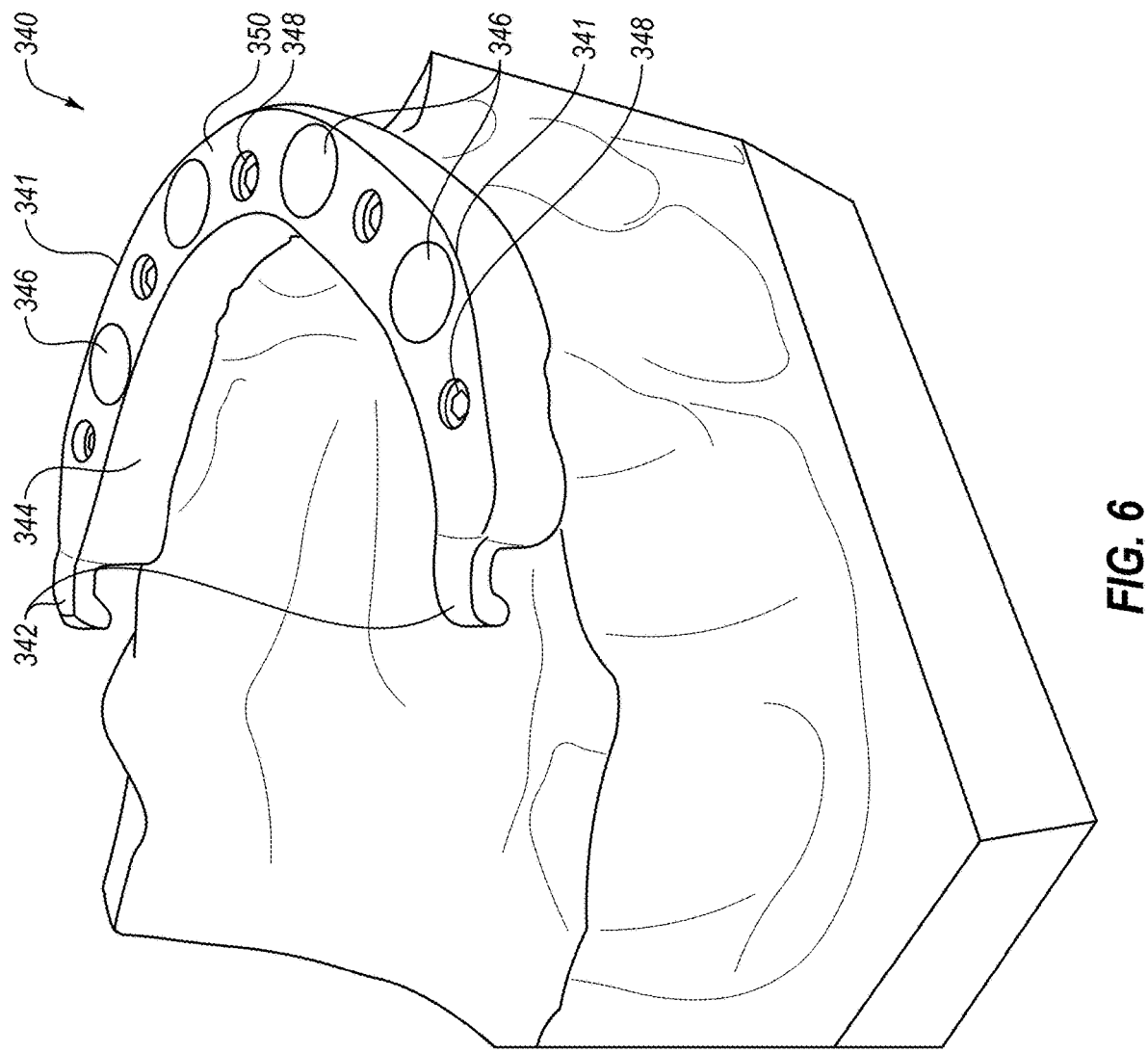
FIG. 6 illustrates a dental implant prosthesis including a bar with distal hinges, in accordance with an embodiment of the present disclosure.

FIG. 6 illustrates a dental implant prosthesis 340 including a bar 341 with distal extensions 342, in accordance with an embodiment of the present disclosure. Bar 341 includes distal extensions 342, a lingual surface 344, an occlusal surface 350 with visible magnets 346, and implant screw access 348.

Figure 15A:
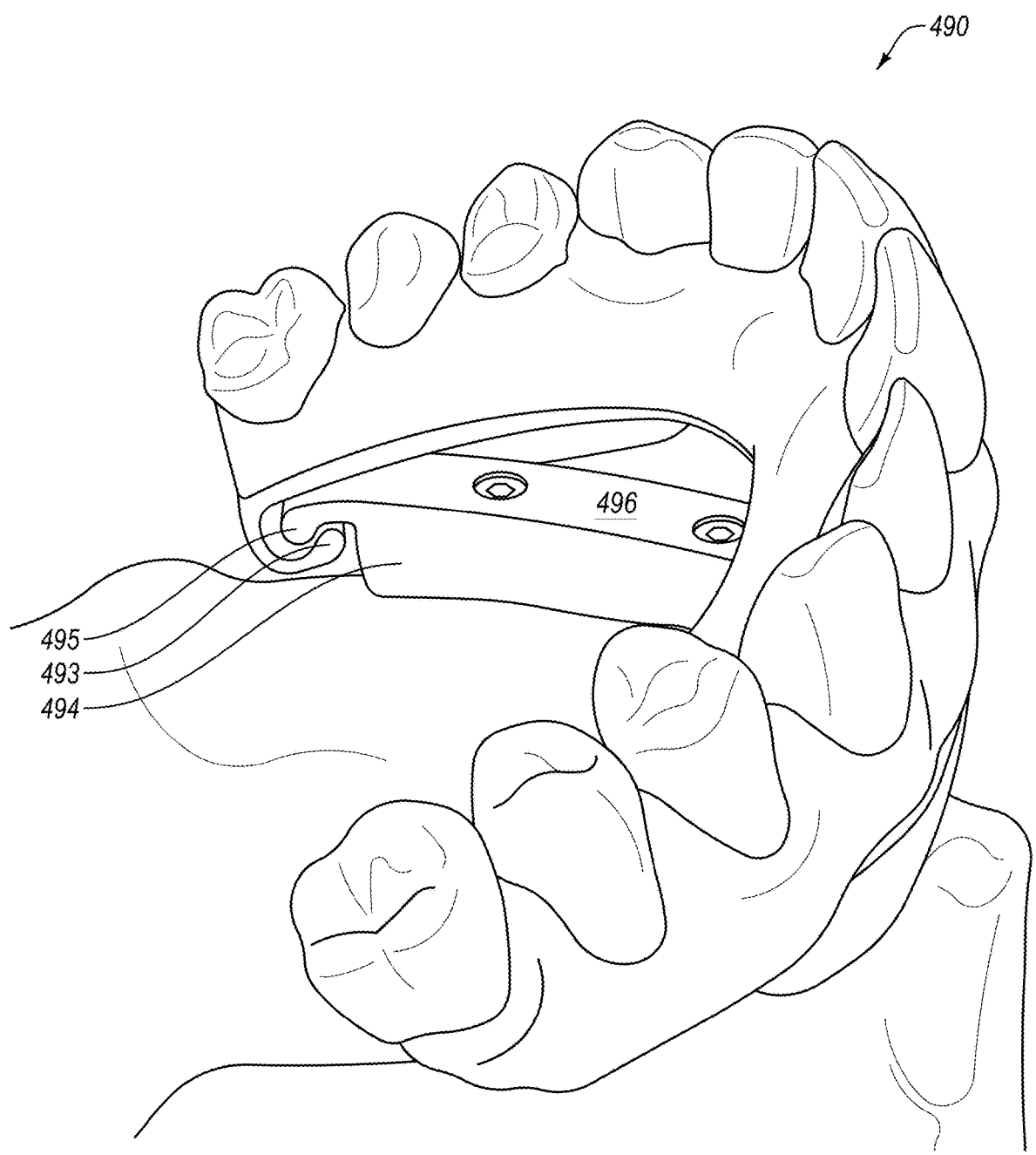
FIGS. 15A and 15B depict a dental device including a dental implant prosthesis and an overdenture, in accordance with an embodiment of the present disclosure.
Figure 15B:
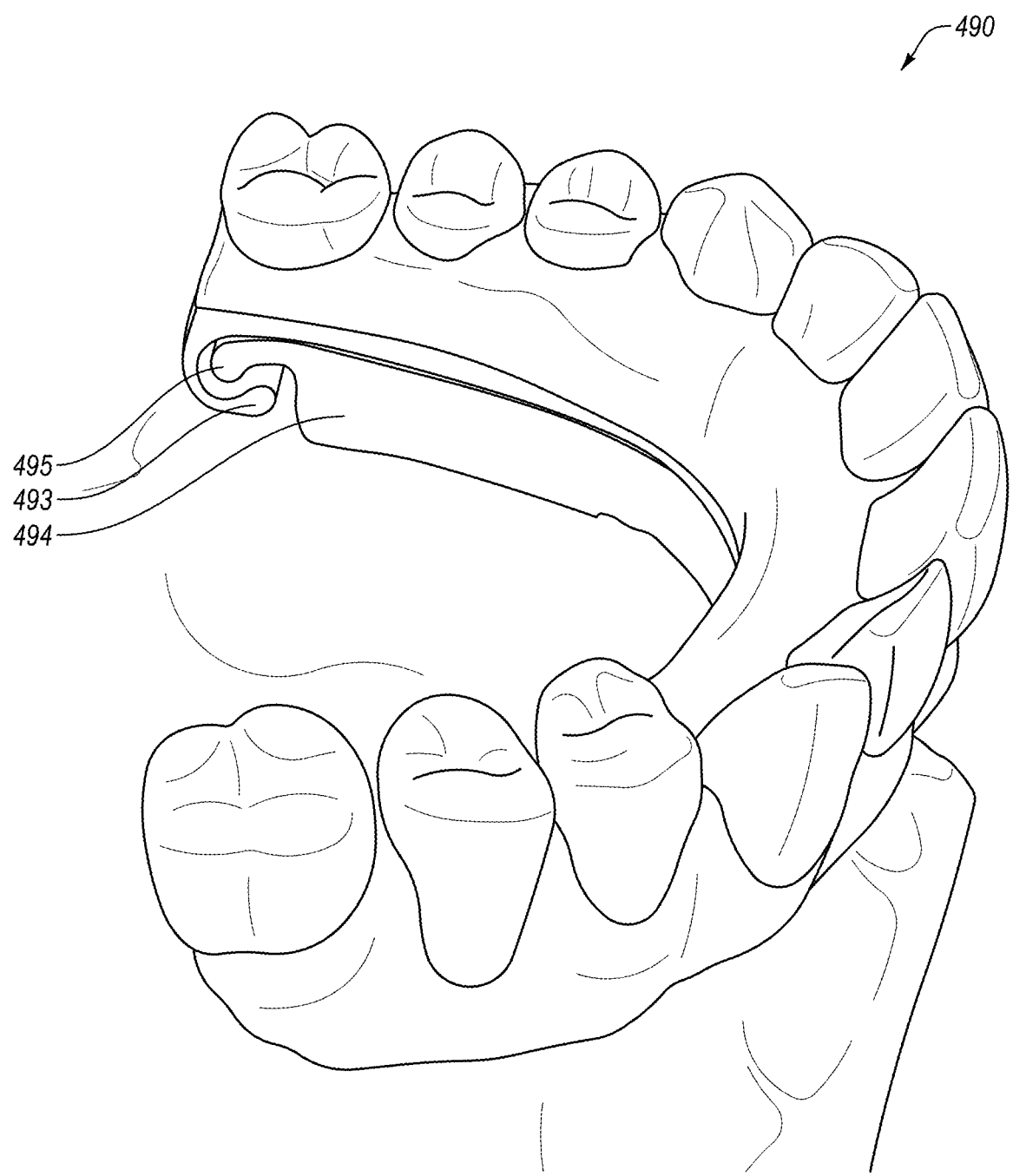
Figure 16A:
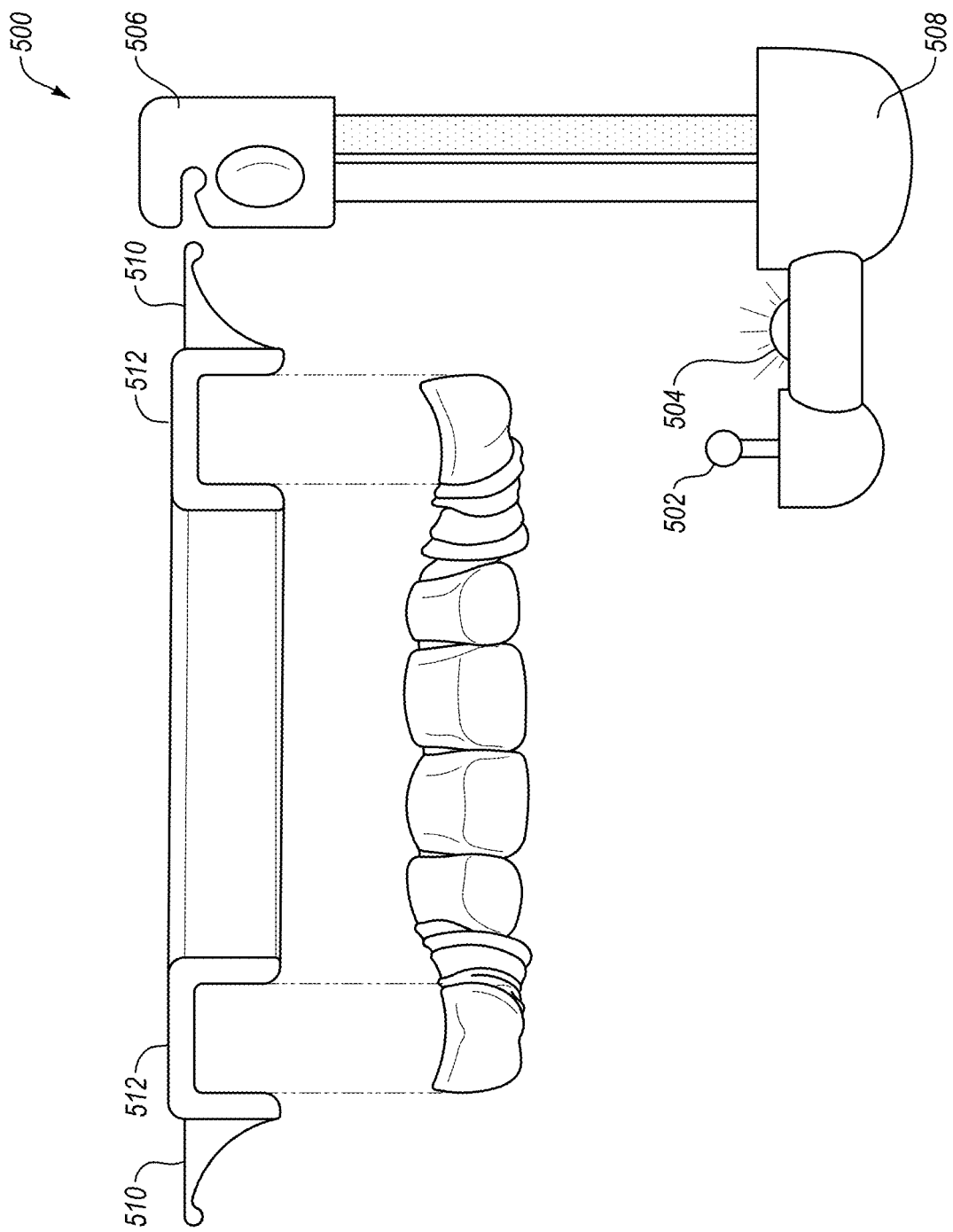
FIG. 16A-16D depict a scanning and drilling device, according to an embodiment of the present disclosure.
Figure 16D:
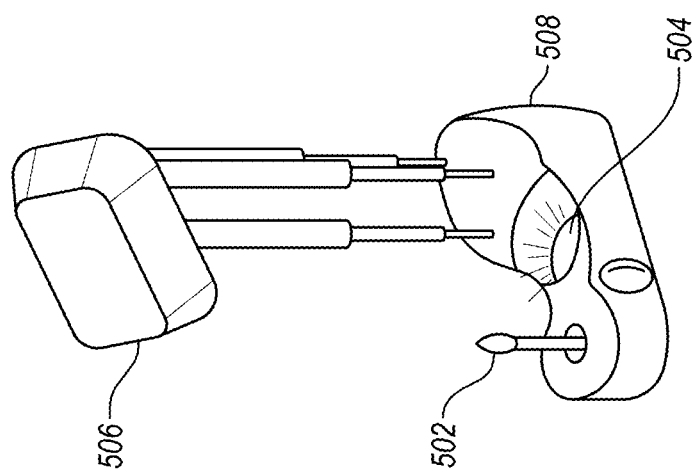
Figure 16C:
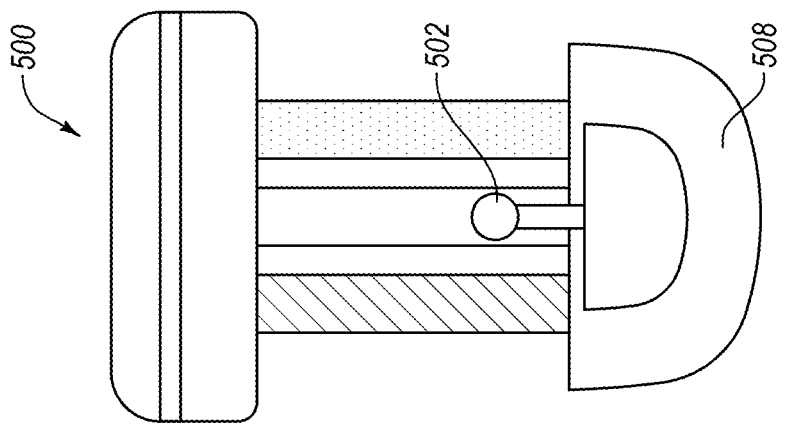
Figure 16B:
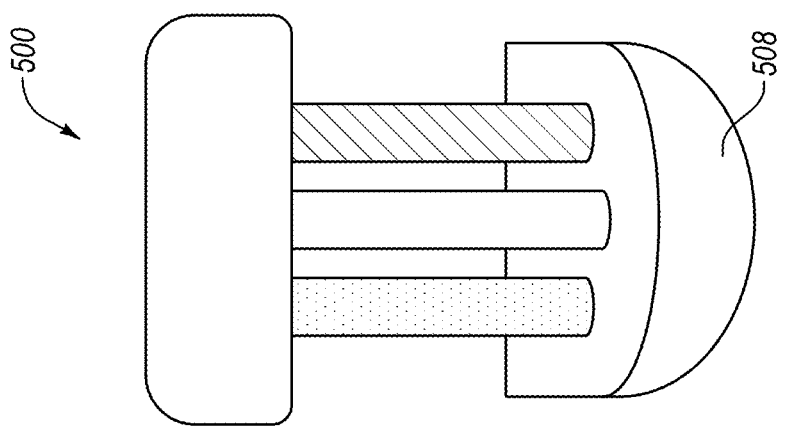

With reference to FIGS. 15A and 15B, a dental device including an overdenture 490 and a bar 494 is illustrated. More specifically, FIG. 15A depicts an overdenture 490 positioned at an angle relative to bar 494 to either insert overdenture 490 (e.g., into a patient's mouth and onto bar 494), or remove overdenture 490 (e.g., off of bar 494 and out of a patient's mouth). FIG. 15B depicts overdenture 490 positioned on and secured to bar 494.

As illustrated in FIG. 15A, while positioning overdenture 490 onto bar 494, overdenture 490 may be positioned at an angle relative to a surface 496 of bar 494. Similarly, overdenture 490 may be positioned at an angle while removing overdenture 490 from bar 494 (e.g., while removing overdenture 490 from a user's mouth). Stated another way, overdenture 490 may be inserted into or removed from a patient's mouth via an angled path of insertion. Further, during insertion, one or more extensions 495 on the bilateral distal ends of a bar 494 are configured to engage hinges 493 (illustrated as having a hook-shaped extension) of overdenture 490 as a pivot point, lock overdenture 490 in place, and resist vertical dislodgement. During removal, upon overdenture being positioned at an angle relative to surface 496, hinge 493 may rotate and disengage from extension 495, thus, allowing overdenture 490 to be removed.

Other embodiments of a denture device include one or more implant abutments, which can be used in combination with a number of denture attachment systems. Implant abutments may be used bilaterally on the posterior-most implants and in combination with one or more denture attachment systems on the anterior implant abutments. An implant abutment may include one or more extensions configured to secure to one or more hinges of an overdenture. In one embodiment, an overdenture may have a specific path of insertion (i.e., into a patient's mouth), may rotate on an extension of one or more abutments, and secure into place on the one or more abutments. Further, a dental device including one or more abutments may include one or more attachment systems such as, but not limited to, clips, O-rings, locator attachments, pin systems, and/or magnetic attachment systems.

Figure 7:
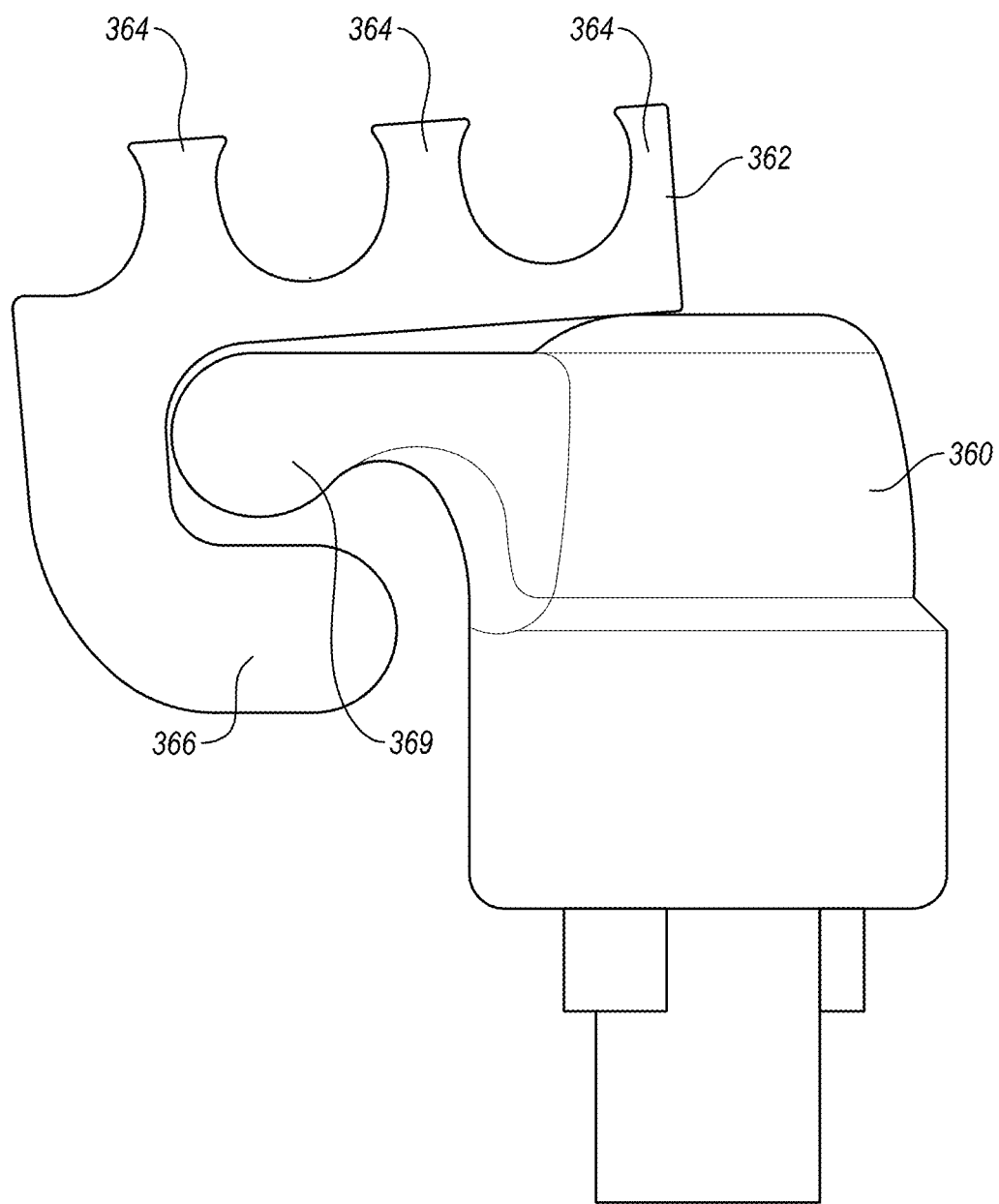
FIG. 7 depicts a hinge abutment and a dental substructure, according to an embodiment of the present disclosure.

FIG. 7 depicts an abutment 360 and a dental substructure 362, according to an embodiment of the present disclosure. It is noted that substructure 362 may be part of an overdenture (e.g., overdenture 320 of FIG. 5). Substructure 362 includes retention grooves 364 and a hinge 366. Abutment 360 comprises an implant abutment with extension 369. As will be appreciated, substructure 362 may have a specific angled path of insertion (i.e., into a patient's mouth), which may enable hinge 366 to contact and rotate on extension 369. Hinge 366 and extension 369 may aid in preventing undesirable movement of an overdenture within a patient's mouth. Further, substructure 362 may be further secured into place on the one or more abutments using a variety of attachment systems such as, but not limited to, clips, O-rings, locator attachments, pin systems, and/or magnetic attachment systems.

An overdenture including substructure 362 may be removed from the mouth by rotating hinge 366 (i.e., the opposite direction for insertion) about extension 369 to disengage hinge 366 from extension 369 and removing the overdenture at an angled path of removal, which may be the opposite of, but substantially similar to, the angled path of insertion.

Figure 8A:
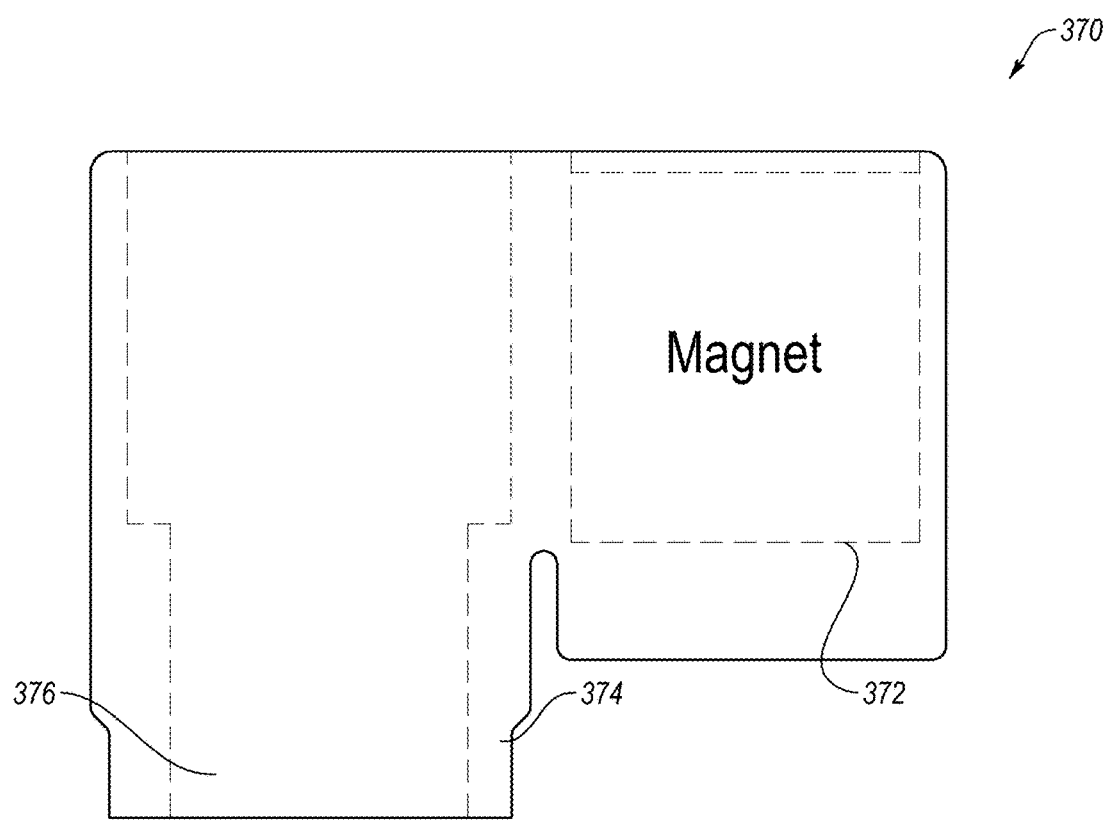
FIGS. 8A and 8B depict an abutment, in accordance with an embodiment of the present disclosure.
Figure 8B:
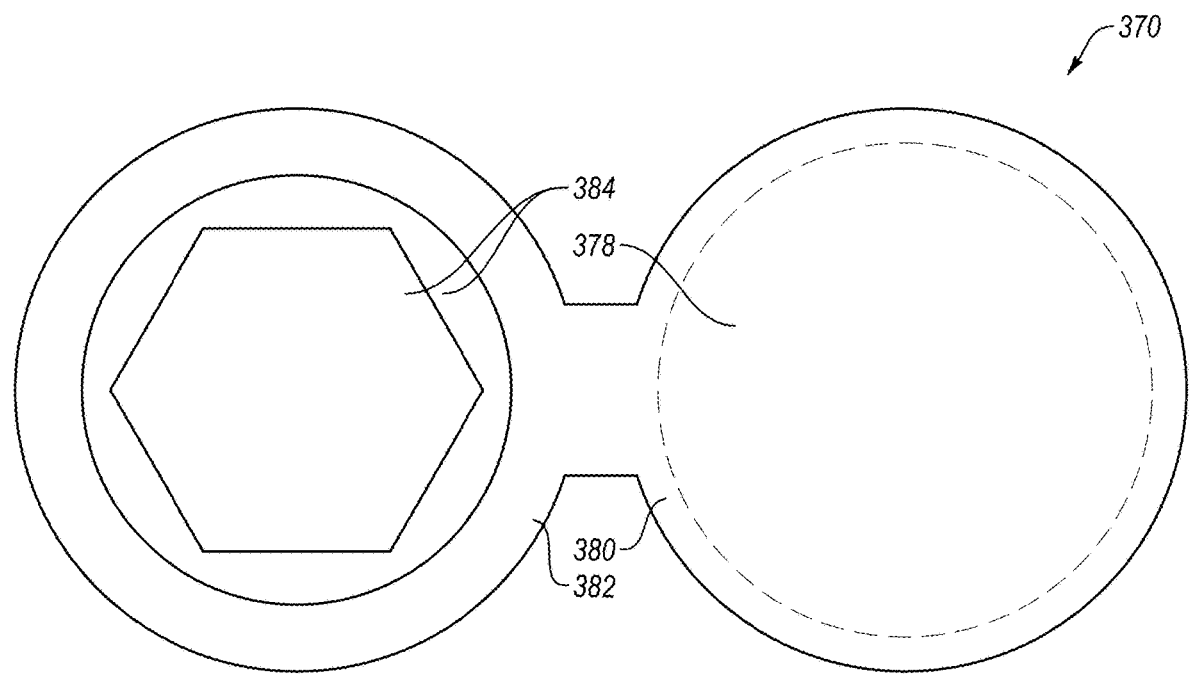
Figure 9A:
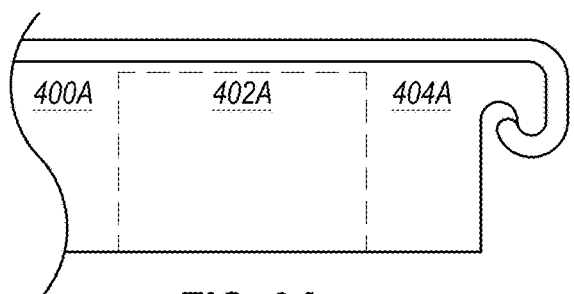
FIGS. 9A-9J illustrate example extensions on a dental implant prosthesis, in accordance with various embodiments of the present disclosure.
Figure 9B:
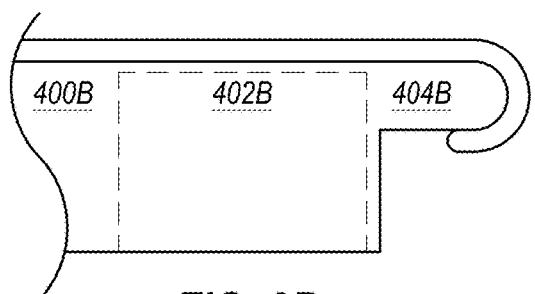
Figure 9C:
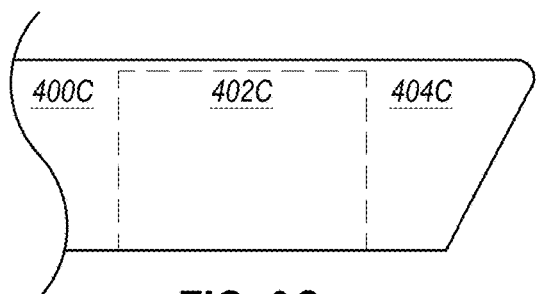
Figure 9D:
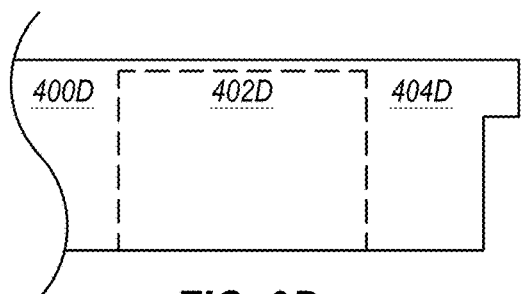
Figure 9E:
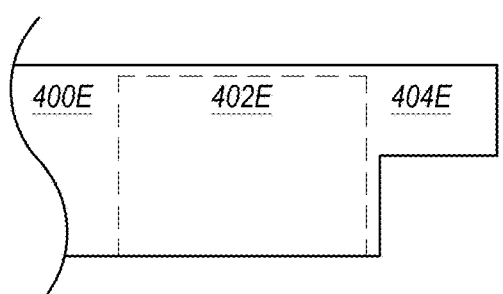
Figure 9F:
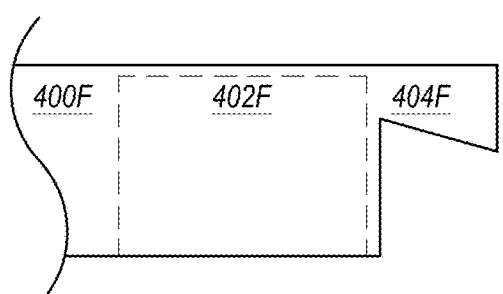
Figure 9G:
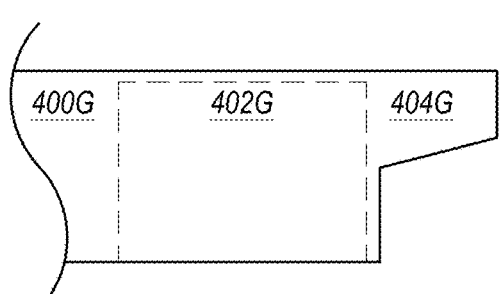
Figure 9H:
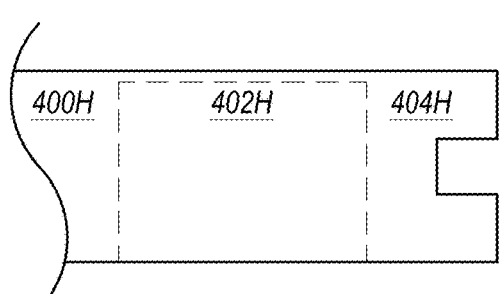
Figure 9I:
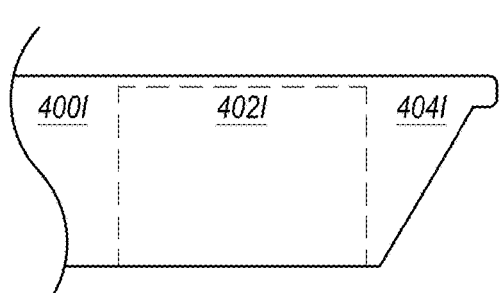
Figure 9J:
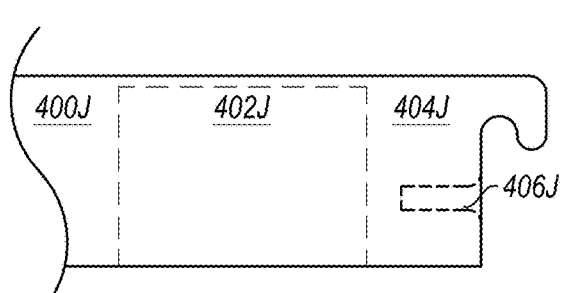

FIGS. 8A and 8B depict an abutment 370, in accordance with an embodiment of the present disclosure. As illustrated in FIG. 8A, which is a lateral view, abutment 370 includes a cantilever off implant abutment containing magnet 372, an implant abutment (e.g., a screw-retained (titanium) magnetic abutment) 374, and an abutment attachment device (e.g., screw) 376. Further, as illustrated in FIG. 8B, which is a occlusal view, abutment 370 includes a magnet 378, cantilever off implant abutment containing magnet 380, an implant abutment (e.g., titanium screw-retained magnetic implant abutment) 382, and an abutment attachment device (e.g., screw) 384.

It is noted that distal extensions of a dental implant prosthesis (e.g., a bar or an abutment) may be, for example only, sloped/angled, ledge-like, steplike, cylindrical-like, dome-shaped, or spherical-like in design. FIGS. 9A-9J illustrate example extensions on dental implant prosthesis (e.g., a bar or an abutment) 400A-400J, in accordance with various embodiments of the present disclosure. Dental implant prosthesis 400A-400J may include a space 402A-402J for a magnet, and a distal extension 404A-404J. Further, in some embodiments, dental implant prosthesis 400J includes an attachment device (e.g., a screw) 406J (see FIG. 9J) to retain a distal extension. As will be understood, FIGS. 9A-9J illustrate examples and the present invention is not so limited and may include other distal extension configurations.

Figure 10A:
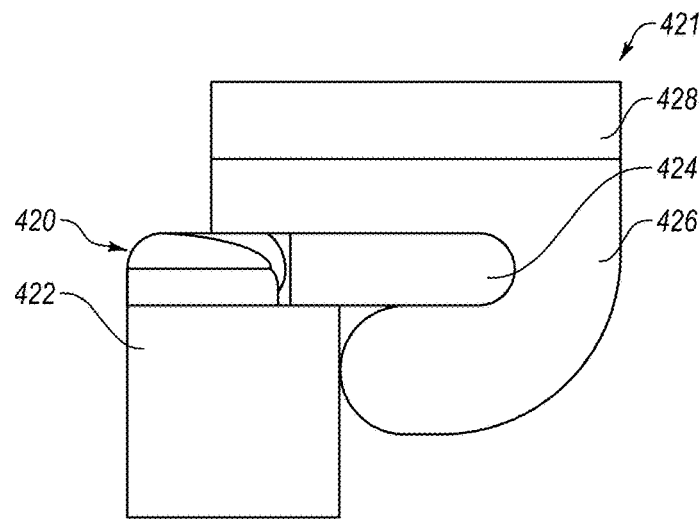
FIGS. 10A-10C depict an implant abutment including a substantially straight distal extension, according to an embodiment of the present disclosure.
Figure 10B:
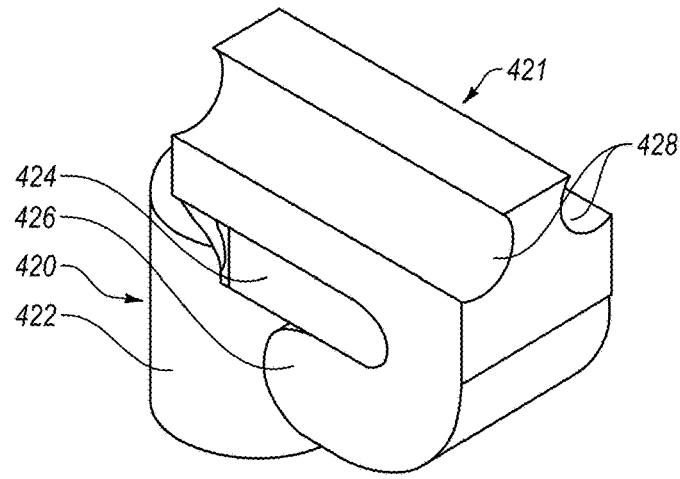
Figure 10C:
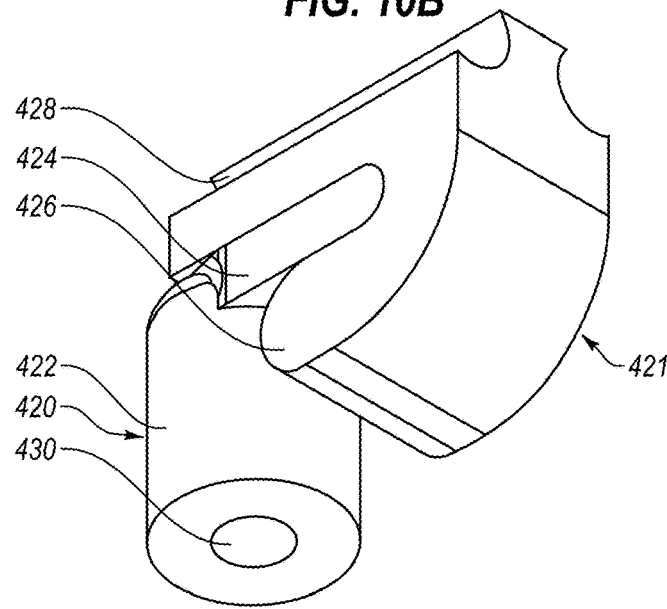

FIGS. 10A-10C depict an implant abutment 420 including a substantially straight distal extensions 424, and a substructure 421, according to an embodiment of the present disclosure. Abutment 420 includes an implant hinge 422 and distal extension 424. Further, substructure 421 includes a distal hinge 426, retentive grooves 428, and a hole 430 for an implant attachment device, such as a screw.

Figure 11A:
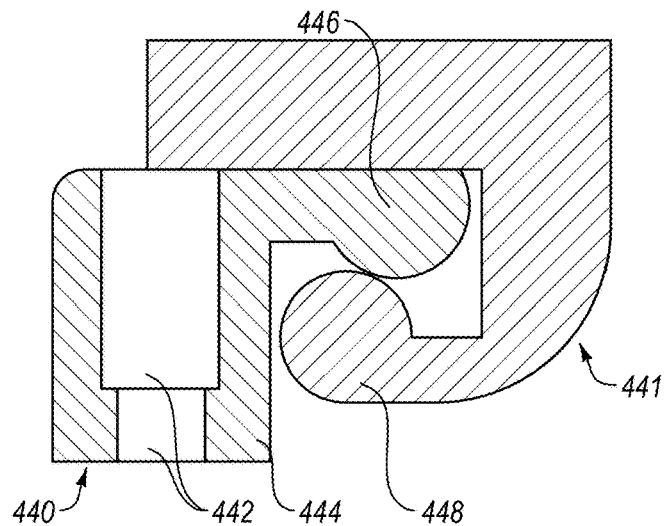
FIGS. 11A-11C depict an implant abutment including a spherical distal extension, according to an embodiment of the present disclosure.
Figure 11B:
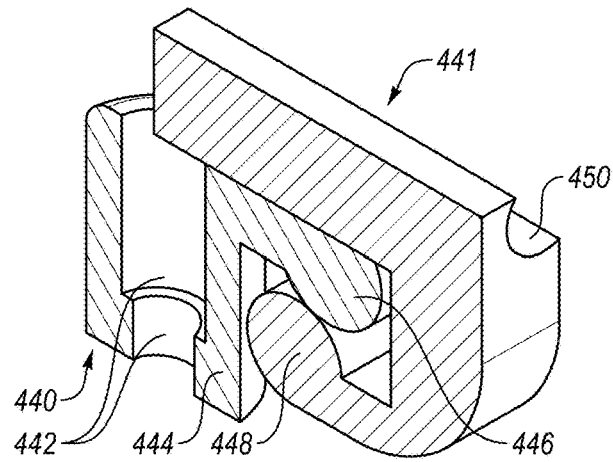
Figure 11C:
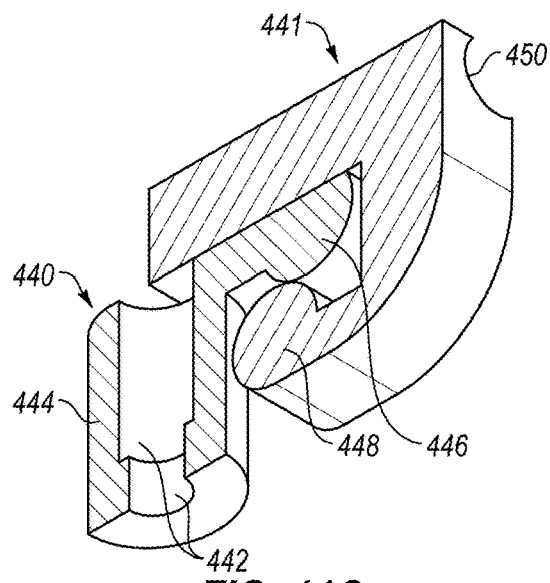

FIGS. 11A-11C depict an implant abutment 440 including a spherical distal extension 446, and a substructure 441, according to an embodiment of the present disclosure. Abutment 440 includes an implant hinge 444, a space 442 for an implant attachment device (e.g., a screw) and distal extension 446. Substructure 441 includes a distal hinge 448 and retentive grooves 450.

Figure 12C:
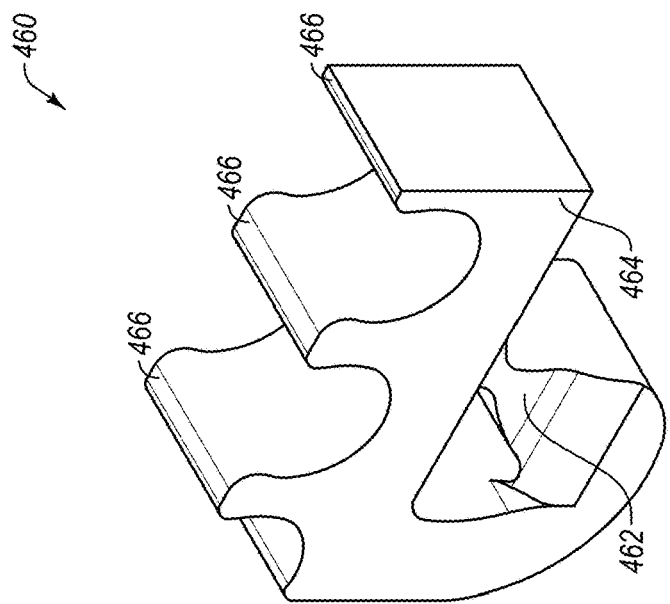
FIGS. 12A-12C illustrate a distal hinge of a dental substructure, in accordance with an embodiment of the present disclosure.
Figure 12B:
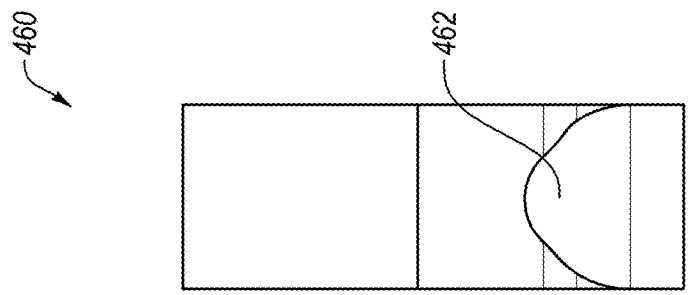
Figure 12A:
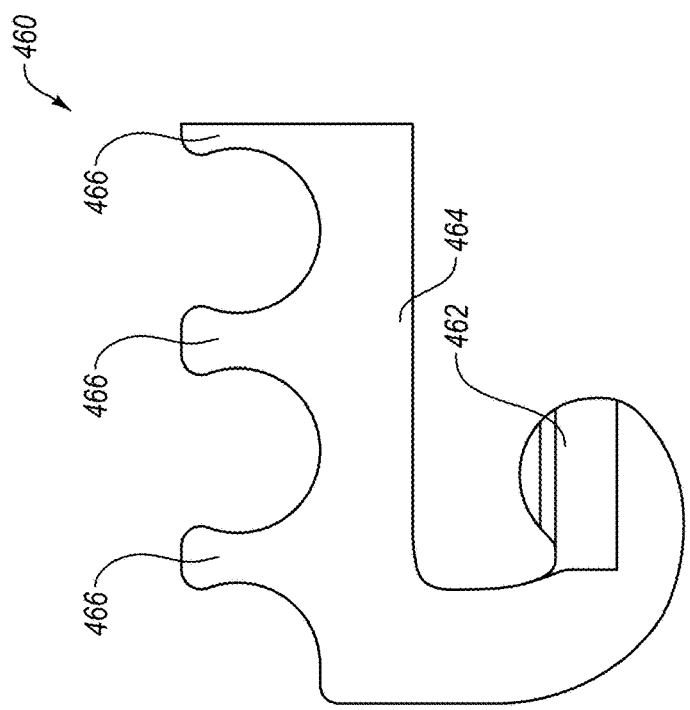

FIGS. 12A-12C illustrate a dental substructure 460, in accordance with an embodiment of the present disclosure. In this embodiment, substructure 460 includes a dome-shaped distal hinge 462, a hinge 464, and retentive grooves 466.

Figure 13A:
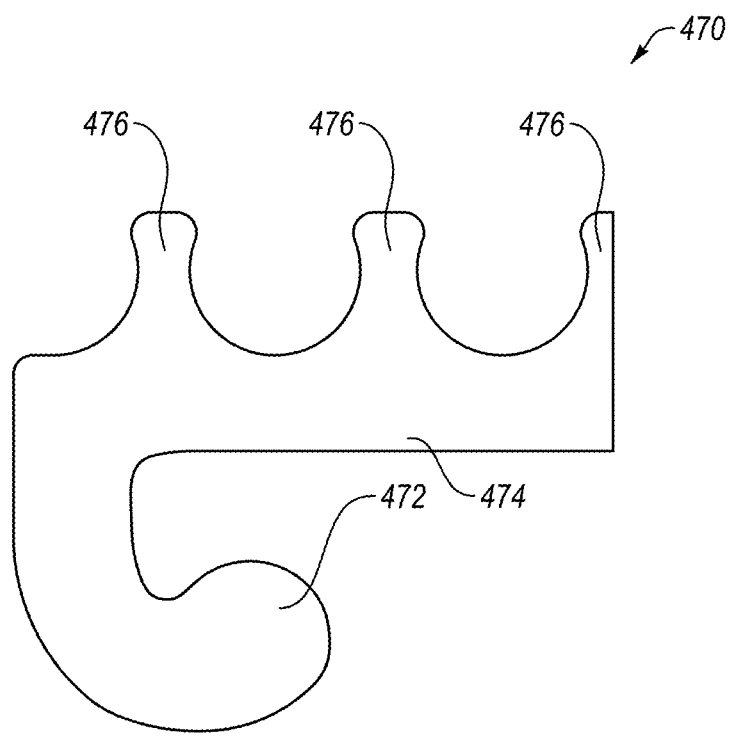
FIGS. 13A and 13B depict another distal hinge of a dental substructure, according to an embodiment of the present disclosure.
Figure 13B:
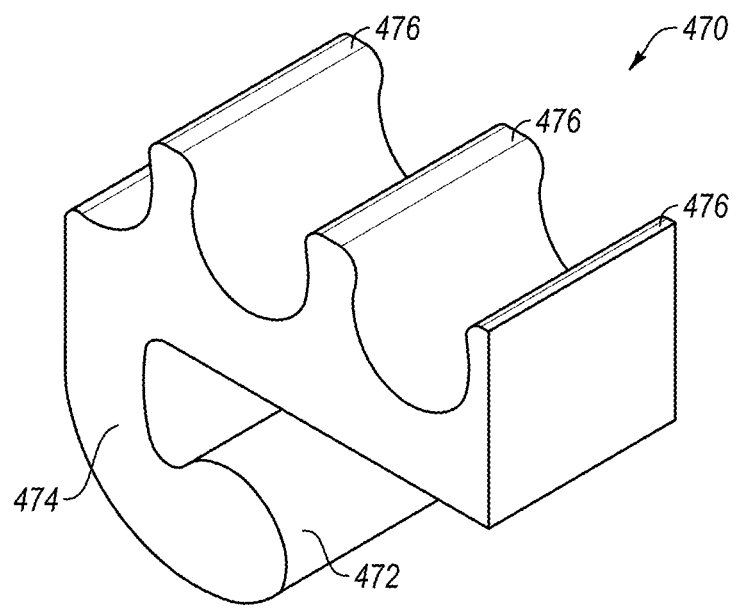

FIGS. 13A and 13B depict another dental substructure 470, according to an embodiment of the present disclosure.

In this embodiment, substructure 470 includes a spherical-shaped distal hinge 472, a hinge 474, and retentive grooves 476.

Figure 14A:
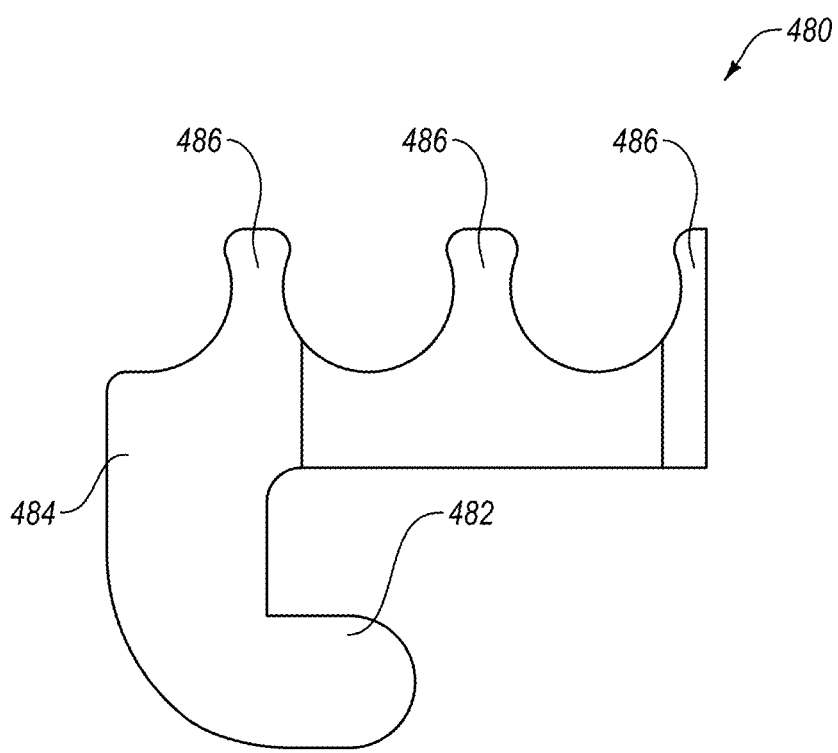
FIGS. 14A and 14B depict yet another distal hinge of a dental substructure, according to an embodiment of the present disclosure.
Figure 14B:
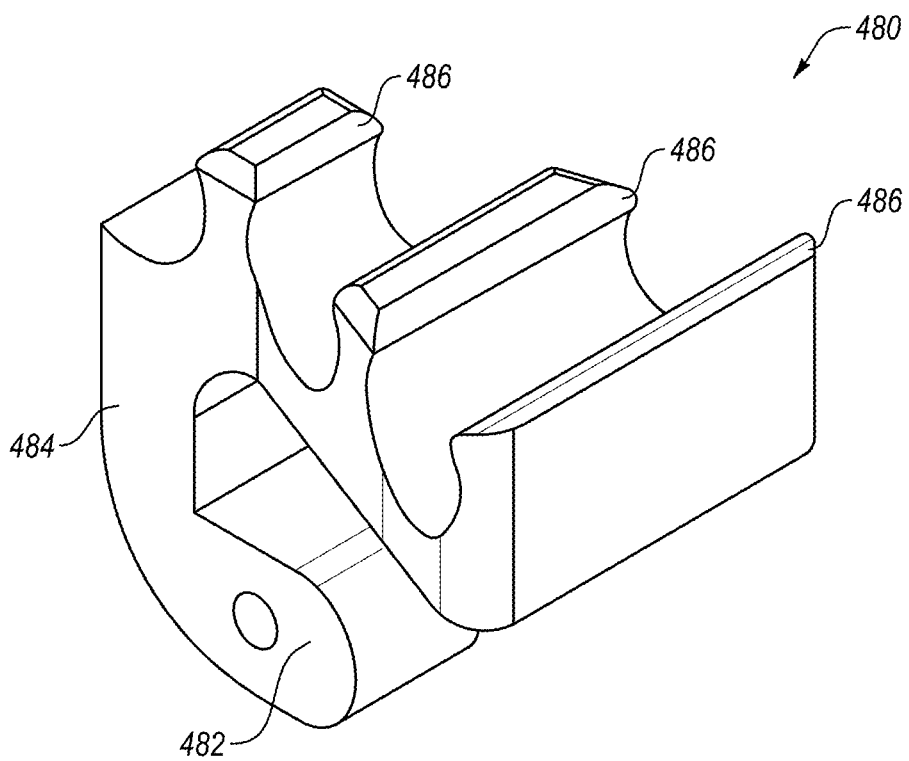

FIGS. 14A and 14B depict yet another distal hinge of a dental substructure 480, according to an embodiment of the present disclosure. In this embodiment, substructure 480 includes round-shaped distal hinge 482, a hinge 484, and retentive grooves 486.

A dental implant prosthesis coupled with an overdenture, in which both contain magnets, allows for the magnet strength to be varied by means of physically separating the magnets away from each other at desired distances (e.g., measured in millimeters) and/or by using different sized & shaped magnets. It is noted that the present disclosure is not limited to magnet-to-magnet configurations. Rather, as will be appreciated by a person having ordinary skill in the art, other configurations (e.g., magnet-to-steel, iron plate, etc.) are contemplated.

As noted above, a dental device may include one or more printable magnets. More specifically, a dental implant prosthesis and/or an overdenture may include one or more printable magnets. As will be understood by a person having ordinary skill in the art, printable magnets may include a north and south field on the same surface. Printable magnets (also referred to herein as "polymagnets") may be configured for extreme strength, and may further be configured for desirable behaviors, such as align, latch, spring and couple. Accordingly, using this technology may enable an overdenture to lock into place with custom printed designs on a dental implant prosthesis (e.g., a bar prosthesis) and/or the overdenture. More specifically, in one embodiment, a dental device may include at least one printable magnet configured for, for example only, a "lock and key" function, which may enable the overdenture to be locked onto an implant bar prosthesis via, for example, rotation of a magnet. It is noted that in this embodiment, a dental device may not require mechanical retention, such as extension, hinges, and/or undercuts. Further, the dental device may not require that an overdenture being inserted at a specific path of insertion, as described herein.

Other embodiments of the present disclosure relate to scanning and drilling devices. In one embodiment, a scanning and drilling device may comprise an automated, removable and programmable scanning and drilling device. A scanning and drilling device may be attached to a screw retained universal guardrail, which may attached to (e.g., screwed into) a facial surface of a bar prosthesis. The scanning and drilling device may be configured for rotating around a patient's dental arch while drilling away unwanted contacts on the occlusal surface of the patient's teeth, thus equilibrating the patient's bite. Since the bite equilibration appointment may be automated with a scanning and drilling device, a dentist may no longer need to manually drill away unwanted contacts.

As will be appreciated, an articulating ribbon has inherent flaws because it shows where unwanted and wanted contacts exist, but not the amount of pressure being applied on each contact. Therefore, a clinician may be required to make an educated guess as to exactly how much tooth structure to drill away when equilibrating the patient's bite. Typically, when there is an imbalance, the imbalance is exploited until the product or system is weakened or fails altogether, or perhaps the patient suffers as a result of an imbalanced occlusion or imperfectly balanced occlusion. An articulating ribbon may not be necessary for the bite equilibration appointment if the patient has internal pressure sensor lined teeth and the teeth are equilibrated with a scanning and drilling device.

In addition, existing pressure sensor technologies, such as Tekscan Inc.'s Digital Occlusal Analysis System have inherent flaws because they may require a patient to bite on a film to determine the amount of force and, thus, the results may not be entirely accurate. These existing pressure sensing technologies may not be necessary for bite equilibration if a patient has internal pressure sensor lined porcelain teeth, and the teeth are equilibrated with a programmable scanning and drilling device.

FIGS. 16A-16D depict a scanning and drilling device 500, according to an embodiment of the present disclosure. As noted above, scanning and drilling device 500 may comprise an automated, removable and programmable scanning and drilling device. Device 500 includes a bur 502, an imaging system 504, a housing 506, and a housing 508. Device 500 may be configured to couple to a guardrail 510, which may be coupled to an implant bar prosthesis 512. In one embodiment, bar prosthesis 512 may include one or more magnets. More specifically, bar prosthesis 512 may be lined with one or more magnets.

Housing 506 may include, for example, a motor system, a hydraulic system, one or more computers, and an attachment apparatus (i.e., for attaching to a universal guardrail 510). Housing 508 may include a motor system, a hydraulic system, an imaging system, bur 502, or any combination thereof. It is noted that bur 502 may be removable.

Figure 17:
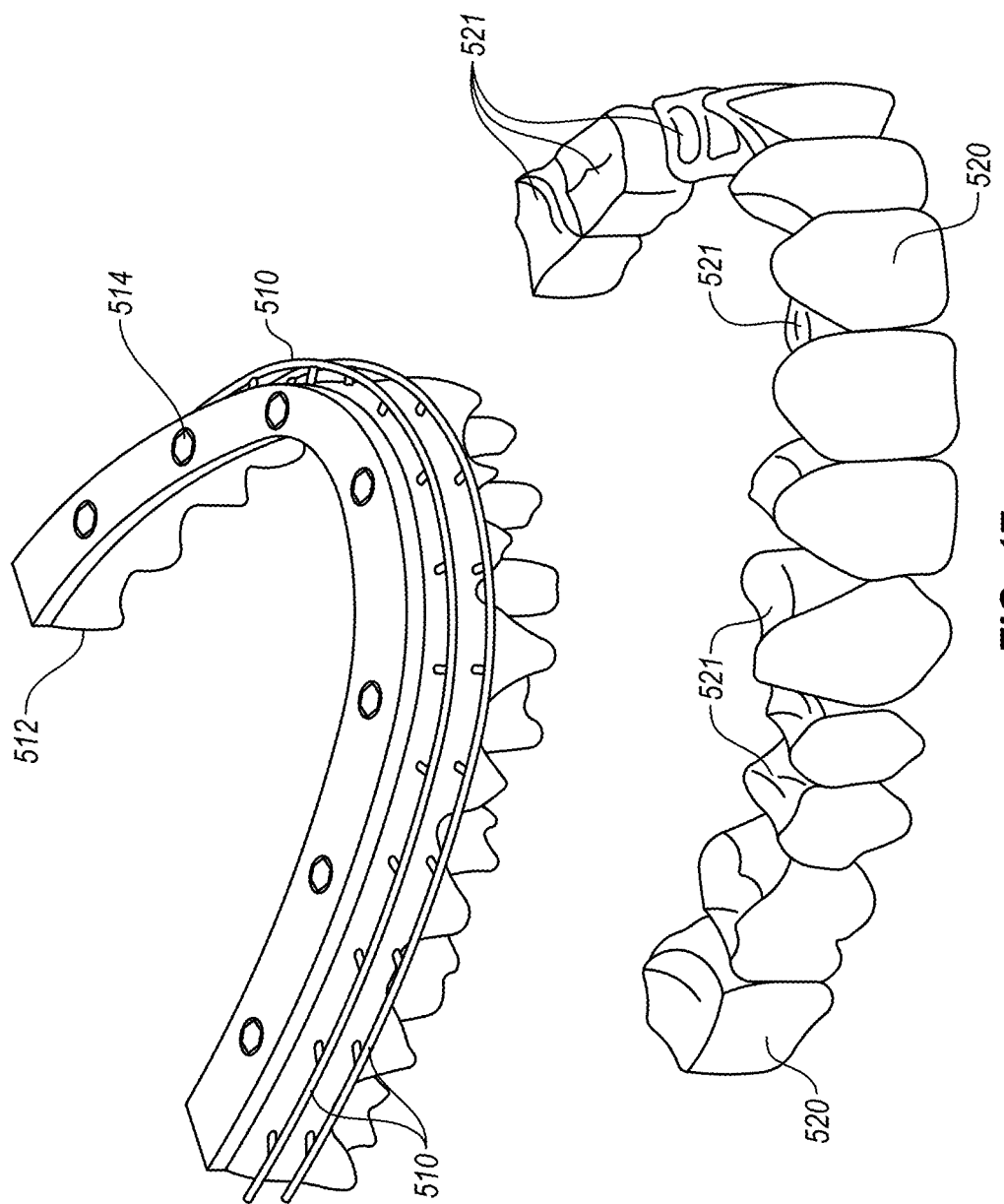
FIG. 17 depicts a guardrail and teeth including pressure sensors, according to an embodiment of the present disclosure.

FIG. 17 depicts a guardrail 510 configured for attaching to bar prosthesis 512, which may attach to teeth 520. In one embodiment, teeth 520 may include one or more pressure sensors 521. In one embodiment, guardrail 510 may be attached to implant bar prosthesis 512 via one or more attachment devices (e.g., screws) via one or more holes 514.

Figure 18:
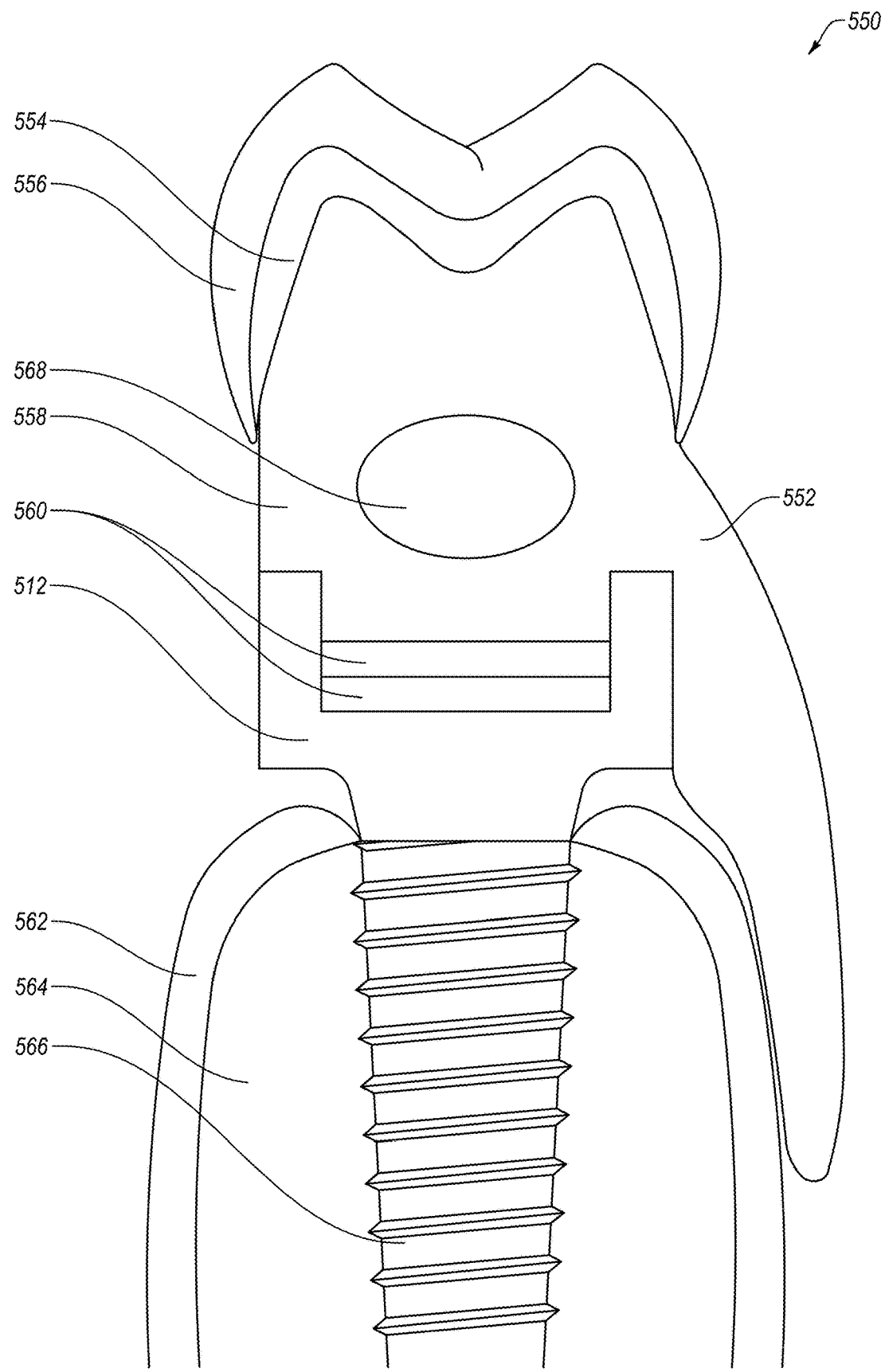
FIG. 18 is a cross-section illustration of a magnetic denture, in accordance with an embodiment of the present disclosure.

FIG. 18 a cross-section illustration of a denture 550, in accordance with an embodiment of the present disclosure. Denture 550 may include a facial flange 552, an internal pressure sensor 554, teeth (e.g., porcelain or denture teeth) 556, a base (e.g., acrylic) 558, one or more magnets 560, implant bar prosthesis 512, Gingiva 562, Alveolar bone 564, and an implant 566. It is noted that implant bar prosthesis 512 may comprise a magnet lined implant bar prosthesis. Further, denture may include a space 568 (e.g., for wearable technology devices and/or wireless transceivers).

Figure 19:
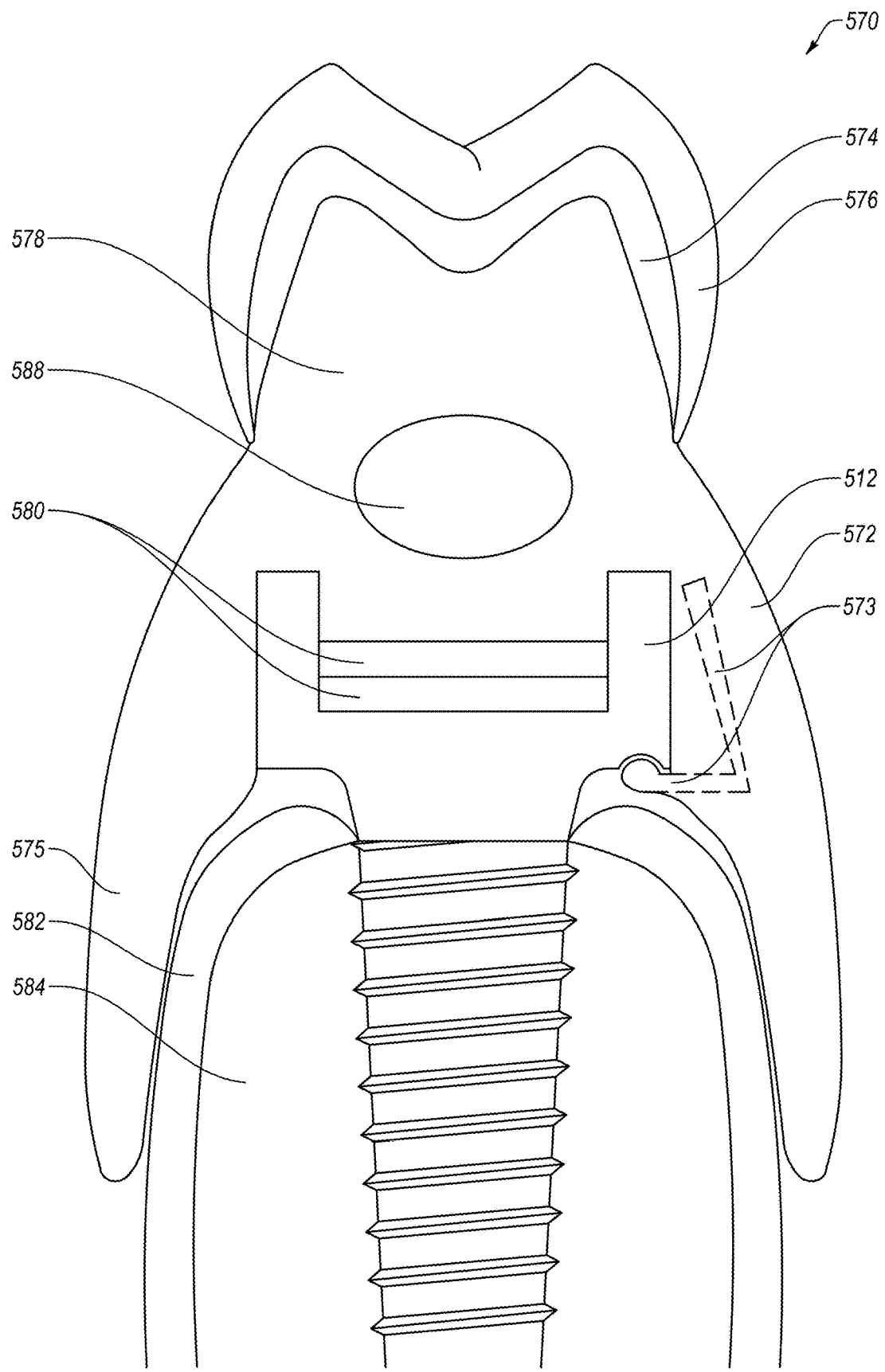
FIG. 19 is another cross-section illustration of a magnetic denture, in accordance with an embodiment of the present disclosure.

FIG. 19 is another cross-section illustration of a denture 570, in accordance with an embodiment of the present disclosure. Denture 570 may include a facial flange (e.g., a flexible flange) 572, a bar 573 incorporated in flange 572, a lingual flange 575, an internal pressure sensor 574, teeth (e.g., porcelain or denture teeth) 576, a base (e.g., acrylic) 578, one or more magnets 580, implant bar prosthesis 512, Gingiva 582, Alveolar bone 584, and an implant 586. It is noted that implant bar prosthesis 512 may comprise a magnet lined implant bar prosthesis. Further, denture 570 may include a space 588 (e.g., for wearable technology devices and/or wireless transceivers).

Wearable technology devices, as disclosed herein, may include, for example, dietary sensors, dehydration sensors, epilepsy sensors, pressure sensor technology, Bluetooth technology, GPS location technology, Glucometer technology, Ketone sensor technology, pH sensors, biological marker sensors, salivary marker sensors, breathalyzer technology, respiratory exchange gases sensor technology, medical alert technology, human vital sign sensor technology, remote control technology, temperature sensor technology, heart rate monitoring technology, real-time locating system technology, breaths per minute monitoring technology, ECG/EKG remote monitoring technology, shock/concussion sensing technology, emergency alert technology, vibration technology, microphone and/or speaker technology, and remote monitoring system technology (e.g., in a cylindrical form of approximately 4.7625 mm in diameter and 4-6 mm in height, or rectangular or square forms of approximately 4.7625 mm×4.7625×3-6 mm in height, or as long strips to be attached either to the lingual surface of the magnetic bar or hybrid denture). It is noted that wearable technology devices may be inserted into a denture through an occlusal surface, a lingual surface, or an inferior surface of the prosthesis.

As will be appreciated, data received from the hybrid denture (i.e., from a technology device) may be transmitted wirelessly to the patient, dentist and/or physician's electronic device (e.g., phone or computer) via mobile phone technology. Further, internal pressure sensor lined teeth may be configured for transmitting data from the internal pressure sensors to an electronic device, which may (e.g., via an application program stored on the electronic) display an amount of force applied to each contact on a 3D model of the patient's dental arch. With information such as where and how much force is being applied to each contact, following the patient biting and clenching his/her teeth together, a scanning and drilling device may be programmed to locate and precisely drill away unwanted contacts to such precision that the clinician can equilibrate the patient's bite to equal forces on each contact, without having to manually drill away unwanted contacts.

It is noted that if a patient has a dental device incorporating internal pressure sensor lined teeth, or any other form of incorporated wearable technology, a battery of the dental device may need to be charged from time to time. It is further noted that some of the devices described herein, such as a dental implant prosthesis, as well as the overdenture, may include magnets, which can be detrimental, if not contraindicated, in individuals with wearable, or incorporated, medical devices such as pacemakers and implantable cardioverter defibrillators. Further, magnets corrode; therefore, the magnets may need to be coated with non-corrosive material such as silicone, rubber, or acrylic.

Like other removable hybrid denture configurations on the market, and unlike fixed hybrid dentures, embodiments disclosed herein allow for a patient to remove an overdenture, at will and, therefore, the overdenture and the dental implant prosthesis (e.g., a bar) may be easily cleaned (e.g., with a toothbrush and/or water pik). Further, various embodiments may provide better stability, comfort, speech, bone preservation, and chewing ability.

A contemplated process, according to various embodiments of the present disclosure, will now be described. An entity may work alongside a dentist (e.g., a restorative dentist) to restore a edentulous oral cavity, as well as provide other medical devices via a magnetically and/or mechanically retained overdenture supported by a removable and screw retained magnet lined bar prosthesis, which may be supported by multiple intra oral implants. The entity may receive digital scans or analog impressions of the maxillary and/or mandibular arch (with included implant analogs) that may be digitized to make a removable screw retained and magnet lined titanium bar prosthesis connecting multiple implants in the upper and lower arch. After the digital scan or analog impression, the patient may have implant healing caps screwed into place and the patient may wear an immediate denture while the implants osseointegrate (e.g., for up to 3 months).

For a bite equilibration/prosthesis delivery appointment, the bar prosthesis may be screwed into place and the entity may provide and deliver one or more of its hybrid denture products. If the patient's denture does not incorporate internal pressure sensor lined teeth, the final magnetic denture prosthesis may be delivered and the restorative dentist may equilibrate the patient's bite. It is noted that this denture may or may not include flexible flanges that retain the denture mechanically, depending on whether the bar prosthesis has facial undercuts, or bilateral posterior hinges/extensions. If the denture does incorporate internal pressure sensor lined teeth, the appointment may comprise of equilibrating the patient's bite via a series of steps and instructions and attachment of a removable screw retained universal guardrail that attaches to the facial surface of the magnet lined hybrid implant bar prosthesis (with facial undercuts on the bar prosthesis).

A scanning and drilling device may be attach to the removable screw retained universal guardrail, and the device may be capable of rotating around the removable universal guardrail and, thus, the patient's dental arch. The scanning and drilling device may rotate around the universal guardrail and scan the occlusal surface of the dental arch and relay a 3D rendering/image of the patient's teeth to a computer program. With the scanning and drilling device removed, the patient may go through a series of instructions such as biting, clenching and tapping teeth together through a range of movements, during which data may be obtained from the internal pressure sensor lined teeth showing precisely where and how much pressure is being applied on each contact. This data may be obtained and sent from the internal pressure sensor lined teeth to, for example, the same computer program with the 3D rendering/image of the patient's teeth.

Further, an executed program (e.g., including an algorithm) may render a 3D model of the patient's teeth, displayed on, for example, a mobile tablet or computer, showing precisely where pressure spots are being applied on the occlusal surface of the patient's teeth. Thus, the scanning and drilling device can be programmed to remove (e.g., drill away) all unwanted contacts (stationary and excursive movements considered). The patient may open his/her mouth maximally, cheeks retracted with cheek retractors, and the scanning and drilling device may be attached to the screw retained universal guardrail, which is screwed into the facial surface of the bar prosthesis. While the patient remains opening maximally, the scanning and drilling device may rotate around the screw retained universal guardrail removing all unwanted contacts until the patient's bite is equilibrated equally and desired results are obtained (e.g., equal pressures on each desired contact). Once the bite is equilibrated, the scanning and drilling device may be removed, as well as the screw retained universal guardrail.

Also, wearable technology may be tested and verified to work. The magnet lined hybrid denture prosthesis with incorporated internal pressure sensor lined teeth and other wearable technology may be sent back to the entity for facial flange attachment. The patient's screw retained magnet lined bar prosthesis may be removed and healing caps may be placed on implants, and the patient's immediate denture/interim denture may be worn until the final prosthesis is delivered. After the entity attaches the mechanically retained flexible facial flanges to the magnetic hybrid denture prosthesis, the final product may be delivered to the patient.

If a hybrid denture has internal pressure sensor lined teeth (with or without additional incorporated wearable technology), the patient may return to the dentist for two appointments (bite equilibration and final product delivery) following the VDO & CR bite registration appointment. If the magnetic hybrid denture has denture teeth or porcelain teeth (with no incorporated internal pressure sensors and with or without other wearable technology) and the patient's bite is to be equilibrated manually (i.e., as opposed to the removable programmed scanning and drilling device equilibrating the patient's bite), the patient may return to the dentist for one appointment following the VDO & CR bite registration appointment for the final product delivery and included bite verification/equilibration.

A scanning and drilling device may be used on all cases involving the use of internal pressure sensor lined teeth and the removable screw retained universal guardrail. Stated another way, the scanning and drilling device may be used with any case involving automated bite equilibration. The scanning and drilling device may send and receive data and is configured to manually change burs, perform programmed commands such as scanning and drilling of selected teeth, and is re-chargeable. The scanning and drilling device may be cleaned with, for example, intermediate-level disinfectant towelettes.

The upper housing on the scanning and drilling device includes the upper hydraulic system, the upper motor system, and the attachment apparatus for attaching to the removable screw retained universal guardrail. The lower housing on the programmable scanning and drilling device includes the lower motor system, the lower hydraulic system, the imaging apparatus, and the drill and bur. The upper hydraulic system is configured to move the device in a vertical direction, while the upper motor system is configured to move the device in a horizontal direction along the screw retained universal guardrail. The lower hydraulic system may be configured to move the drill, bur, and imaging apparatus in a vertical direction while the lower motor system is configured to power the rotating bur. The scanning and drilling device may be used as the "key" for automating the bite equilibration appointment, and without this device, the bite equilibration must be performed manually.

After the scanning and drilling device equilibrates the patient's occlusion, the device may be removed and the patient may go through the same series of instructions such as biting, clenching, and tapping teeth together through a range of movements. As information is transferred from the dental device to a computer, results may show how much pressure is being applied to each contact and where the contact is precisely. If the occlusion is still uneven and, hence, there are still discrepancies in the pressure being applied to each contact, following the series of instructions and biting exercises, the scanning and drilling device may be reprogrammed and re-attached as well as the screw retained universal guardrail for further bite equilibration. When bite equilibration is sufficient (i.e., according to the data), the scanning and drilling device may be removed, as well as the screw retained universal guardrail. Bite equilibration may be complete once sufficient data verifies an equilibrated bite/equilibrated contacts/desired pressure on each contact.

The hybrid denture may then be sent to the entity for facial flange attachment. Once the flanges are attached, and all incorporated wearable technology is shown to be working, the product is finished and ready for delivery. If the patient's denture includes internal pressure sensors inside the teeth, or any wearable technology requiring the use of an electrical charge, a charging device may be provided to charge the patient's denture device.

Embodiments disclosed herein relate a more versatile and easier-to-use dental device for both a dentist and the patient. The overdenture may be easily inserted and removed from the mouth (e.g., by a dentist or a patient), resulting in a device that is easier to use for both a dentist and a patient, and less expensive to manufacture. The dental device does not require abutments and attachments, as opposed to existing removable hybrid dentures, which commonly include o-rings, clips, locator attachments, and/or pin systems. Similarly, the bar prosthesis lacks removable attachments, which are commonly used on existing screw retained hybrid implant bars (i.e., for standard removable hybrid dentures). Further, embodiments of the present disclosure may result in a denture device with verifiable data showing an unquestionably balanced occlusion, without the use of articulating ribbon or pressure sensing film. Further, embodiments may result in less clinical work for the restorative dentist and less time spent in the dental office for the patient.

Figure 20:
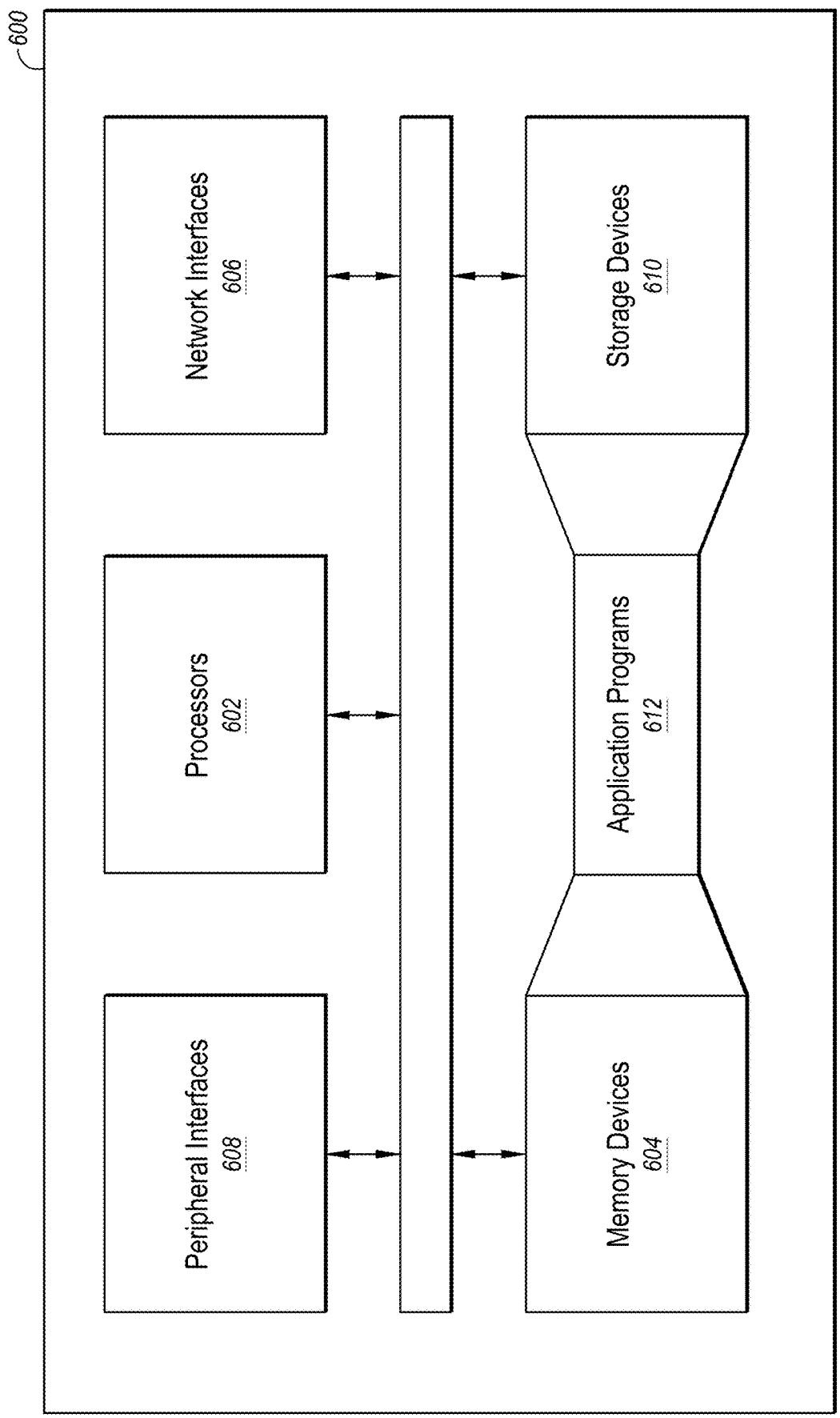
FIG. 20 illustrates a system, in accordance with an embodiment of the present disclosure.

Embodiments of the disclosure may also include one or more systems for implementing one or more embodiments disclosed herein. FIG. 20 illustrates a schematic view of a processing system 600, according to an embodiment of the present disclosure. In an example, processing system 600 may be integrated within any suitable computing device. Processing system 600 may include one or more processors 602 of varying core configurations (including multiple cores) and clock frequencies. Processors 602 may be operable to execute instructions, apply logic, etc. It will be appreciated that these functions may be provided by multiple processors or multiple cores on a single chip operating in parallel and/or communicably linked together. In at least one embodiment, processors 602 may comprise and/or include one or more GPUs.

Processing system 600 may also include a memory system, which may be or include one or more memory devices and/or computer-readable media 604 of varying physical dimensions, accessibility, storage capacities, etc. such as flash drives, hard drives, disks, random access memory, etc., for storing data, such as images, files, and program instructions for execution by processors 602. In an embodiment, computer-readable media 604 may store instructions that, when executed by processors 602, are configured to cause processing system 600 to perform operations. For example, execution of such instructions may cause processing system 600 to implement one or more embodiments described herein.

Processing system 600 may also include one or more network interfaces 606, which may include any hardware, applications, and/or other software. Accordingly, network interfaces 606 may include Ethernet adapters, wireless transceivers, PCI interfaces, and/or serial network components, for communicating over wired or wireless media using protocols, such as Ethernet, wireless Ethernet, etc.

Processing system 600 may further include one or more peripheral interfaces 608, for communication with a display screen, projector, keyboards, mice, touchpads, sensors, other types of input and/or output peripherals, and/or the like. In some implementations, the components of processing system 600 need not be enclosed within a single enclosure or even located in close proximity to one another, but in other implementations, the components and/or others may be provided in a single enclosure.

Memory device 604 may be physically or logically arranged or configured to store data on one or more storage devices 610. Storage device 610 may include one or more file systems or databases in any suitable format. Storage device 610 may also include one or more application programs 612, which may contain interpretable or executable instructions for performing one or more of the disclosed processes. When requested by processors 602, one or more of the application programs 612, or a portion thereof, may be loaded from storage devices 610 to memory devices 604 for execution by processors 602.

Those skilled in the art will appreciate that the above-described componentry is merely one example of a hardware configuration, as the processing system 600 may include any type of hardware components, including any necessary accompanying firmware or software, for performing the disclosed implementations. Processing system 600 may also be implemented in part or in whole by electronic circuit components or processors, such as application-specific integrated circuits (ASICs) or field-programmable gate arrays (FPGAs).

Although the foregoing description contains many specifics, these should not be construed as limiting the scope of the disclosure or of any of the appended claims, but merely as providing information pertinent to some specific embodiments that may fall within the scopes of the disclosure and the appended claims. Features from different embodiments may be employed in combination. In addition, other embodiments may also be devised which lie within the scopes of the disclosure and the appended claims. The scope of the disclosure is, therefore, indicated and limited only by the appended claims and their legal equivalents. All additions, deletions and modifications to the disclosure, as disclosed herein, that fall within the meaning and scopes of the claims are to be embraced by the claims.

What is claimed is:

1. A dental device, comprising:
   a bar configured to be attached to a jawbone and including:
   at least one magnet proximate an outer, occlusal surface of the bar; and
   at least one distal extension extending from the occlusal surface and including at least a portion configured to extend from the occlusal surface in a direction substantially perpendicular to the occlusal surface and toward the jawbone while the bar is attached to the jawbone; and
   an overdenture including at least one hook-shaped extension at a distal end of the overdenture and extending from a planar, inferior surface of the overdenture, the at least one hook-shaped extension being fixed relative to the planar, inferior surface of the overdenture, the at least one hook-shaped extension configured to:
   contact an exterior end surface of the at least one distal extension of the bar;
   secure the overdenture to the bar upon being rotated about the exterior end surface of the at least one distal extension of the bar in a first direction such that the planar, inferior surface of the overdenture abuts the occlusal surface of the bar; and
   release the overdenture upon being rotated about the exterior end surface of the at least one distal extension of the bar in a second, different direction such that the planar, inferior surface of the overdenture is at an angle relative to the occlusal surface of the bar.

2. The dental device of claim 1, wherein the overdenture comprises at least one material that is attracted to the at least one magnet of the bar.

3. The dental device of claim 1, wherein the bar comprises titanium.

4. The dental device of claim 1, wherein the bar further comprises at least one facial undercut for further securing the overdenture thereto.

5. The dental device of claim 1, wherein the at least one distal extension of the bar comprises two distal extensions.

6. The dental device of claim 1, wherein the bar further includes at least one technology device integrated therein including at least one of the following: a Bluetooth device, a GPS location device, a remote control device, a temperature sensor device, a real-time locating device, a shock/concussion sensing device, an emergency alert device, a vibration device, a microphone, a speaker, and a remote monitoring device.

7. The dental device of claim 1, wherein the at least one distal extension of the bar comprises one of a sloped configuration, a ledge configuration, a step configuration, a cylindrical configuration, a dome-shaped configuration, and a spherical configuration.

* * * * *

UNITED STATES PATENT AND TRADEMARK OFFICE
CERTIFICATE OF CORRECTION

PATENT NO. : 10,543,068 B2
APPLICATION NO. : 15/089796
DATED : January 28, 2020
INVENTOR(S) : Nathan Stobbe et al.

Page 1 of 1

It is certified that error appears in the above-identified patent and that said Letters Patent is hereby corrected as shown below:

In the Specification
Column 6, Line 35, change "steplike," to --step-like,--

Signed and Sealed this
Third Day of March, 2020

Andrei Iancu
*Director of the United States Patent and Trademark Office*